US012599471B2

(12) United States Patent (10) Patent No.: US 12,599,471 B2

Gifford, III et al. (45) Date of Patent: Apr. 14, 2026

(54) EXPANDABLE DEVICES AND ASSOCIATED SYSTEMS AND METHODS

(71) Applicant: The Foundry, LLC, Menlo Park, CA (US)

(72) Inventors: Hanson S. Gifford, III, Woodside, CA (US); Edward DeWitt Gifford, Glastonbury, CT (US); Vrad W. Levering, Smithville, TX (US)

(73) Assignee: The Foundry, LLC, Menlo Park, CA (US)

( * ) Notice: Subject to any disclaimer, the term of this patent is extended or adjusted under 35 U.S.C. 154(b) by 702 days.

(21) Appl. No.: 17/907,005

(22) PCT Filed: Mar. 24, 2021

(86) PCT No.: PCT/US2021/070306

§ 371 (c)(1),
(2) Date: Sep. 22, 2022

(87) PCT Pub. No.: WO2021/195664

PCT Pub. Date: Sep. 30, 2021

(65) Prior Publication Data

US 2023/0115137 A1 Apr. 13, 2023

Related U.S. Application Data

(60) Provisional application No. 62/993,845, filed on Mar. 24, 2020.

(51) Int. Cl.
*A61F 2/91* (2013.01)
*A61F 2/06* (2013.01)
*A61F 2/24* (2006.01)

(52) U.S. Cl.
CPC .............. *A61F 2/06* (2013.01); *A61F 2/2418* (2013.01)

(58) Field of Classification Search
CPC ........ A61F 2002/825; A61F 2002/9505; A61F 2002/9155–2002/91591; A61F 2/91; A61F 2/24; A61F 2/2418
See application file for complete search history.

(56) References Cited

U.S. PATENT DOCUMENTS

| 5,496,365 A | * | 3/1996 | Sgro | ....................... A61F 2/915 |
| | | | | 623/1.2 |
| 5,591,197 A | | 1/1997 | Orth et al. | |

(Continued)

FOREIGN PATENT DOCUMENTS

| CA | 2634358 A1 | * | 6/2007 | ........... A61F 2/2418 |
| CN | 101959478 A | | 1/2011 | |

(Continued)

OTHER PUBLICATIONS

International Search Report and Written Opinion dated Jul. 29, 2021; International Application No. PCT/US21/70306; 14 pages.

*Primary Examiner* — Alvin J Stewart

(74) *Attorney, Agent, or Firm* — FORTEM IP LLP

(57) ABSTRACT

Devices, systems, and methods for treating a blood flow passage are disclosed herein. For example, expandable devices of the present technology may comprise a stent having a collapsed configuration for delivery through a delivery device to a treatment site in a body conduit and an expanded configuration. The stent may comprise a plurality of struts and longitudinally extending first and second spines configured to move in opposing axial directions as the stent expands. Each of the struts may extend between and connect one of the first spines and one of the second spines. Moving the first spines axially relative to the second spines may cause the struts to push circumferentially adjacent spines to move away from one another, thereby increasing a diameter of the stent.

32 Claims, 20 Drawing Sheets

(56) References Cited

U.S. PATENT DOCUMENTS

| | | | | |
|---|---|---|---|---|
| 5,681,346 | A | 10/1997 | Orth et al. | |
| 5,733,325 | A * | 3/1998 | Robinson | A61F 2/07 |
| | | | | 623/1.11 |
| 5,735,871 | A * | 4/1998 | Sgro | A61F 2/82 |
| | | | | 606/198 |
| 5,853,419 | A * | 12/1998 | Imran | A61F 2/915 |
| | | | | 606/198 |
| 6,206,910 | B1 * | 3/2001 | Berry | A61F 2/91 |
| | | | | 623/1.15 |
| 6,206,916 | B1 * | 3/2001 | Furst | A61F 2/91 |
| | | | | 623/1.46 |
| 7,118,600 | B2 * | 10/2006 | Dua | A61F 2/04 |
| | | | | 623/23.64 |
| 7,815,673 | B2 * | 10/2010 | Bloom | A61F 2/915 |
| | | | | 623/1.15 |
| 8,114,152 | B2 * | 2/2012 | Furst | A61L 31/16 |
| | | | | 623/1.45 |
| 8,696,729 | B2 * | 4/2014 | Thompson | A61F 2/966 |
| | | | | 623/1.11 |
| 8,894,702 | B2 * | 11/2014 | Quadri | A61F 2/2403 |
| | | | | 623/1.36 |
| 10,238,339 | B2 | 3/2019 | Dlugach et al. | |
| 10,470,881 | B2 * | 11/2019 | Noe | A61F 2/2412 |
| 10,925,706 | B2 * | 2/2021 | Eigler | A61M 27/002 |
| 11,291,807 | B2 * | 4/2022 | Eigler | A61F 2/91 |
| 11,812,930 | B2 * | 11/2023 | Jen | A61F 2/04 |
| 11,850,138 | B2 * | 12/2023 | Eigler | A61F 2/01 |
| 2001/0011188 | A1 * | 8/2001 | Berry | A61F 2/91 |
| | | | | 623/1.16 |
| 2002/0052646 | A1 | 5/2002 | Fischell et al. | |
| 2002/0055767 | A1 * | 5/2002 | Forde | A61F 2/962 |
| | | | | 623/1.11 |
| 2003/0105517 | A1 | 6/2003 | White et al. | |
| 2005/0038501 | A1 * | 2/2005 | Moore, Jr. | A61F 2/915 |
| | | | | 623/1.2 |
| 2005/0080478 | A1 | 4/2005 | Barongan | |
| 2007/0213813 | A1 * | 9/2007 | Von Segesser | A61F 2/2433 |
| | | | | 623/2.11 |
| 2007/0239261 | A1 * | 10/2007 | Bose | A61F 2/915 |
| | | | | 623/1.15 |
| 2008/0077228 | A1 * | 3/2008 | Goto | A61F 2/91 |
| | | | | 623/1.11 |
| 2008/0234800 | A1 * | 9/2008 | Clarke | A61F 2/915 |
| | | | | 623/1.16 |
| 2009/0248132 | A1 * | 10/2009 | Bloom | A61F 2/852 |
| | | | | 623/1.15 |
| 2009/0248133 | A1 * | 10/2009 | Bloom | A61F 2/91 |
| | | | | 623/1.15 |
| 2009/0270972 | A1 * | 10/2009 | Lane | A61F 2/2418 |
| | | | | 623/1.14 |
| 2010/0174309 | A1 * | 7/2010 | Fulkerson | A61F 2/915 |
| | | | | 606/200 |
| 2011/0106234 | A1 * | 5/2011 | Grandt | A61F 2/86 |
| | | | | 623/1.11 |
| 2011/0238154 | A1 * | 9/2011 | Murphy | A61F 2/91 |
| | | | | 623/1.42 |

| | | | | |
|---|---|---|---|---|
| 2011/0251674 | A1 | 10/2011 | Schmid et al. | |
| 2012/0116498 | A1 | 5/2012 | Chuter et al. | |
| 2014/0180384 | A1 * | 6/2014 | LeBlanc | A61F 2/844 |
| | | | | 623/1.11 |
| 2014/0200655 | A1 * | 7/2014 | Webler, Jr. | A61F 2/2451 |
| | | | | 623/1.1 |
| 2014/0277345 | A1 * | 9/2014 | Havel | A61F 2/9662 |
| | | | | 623/1.11 |
| 2014/0277562 | A1 | 9/2014 | Seddon et al. | |
| 2015/0216552 | A1 | 8/2015 | Hefer | |
| 2015/0265438 | A1 * | 9/2015 | Hossainy | A61L 31/041 |
| | | | | 623/1.11 |
| 2016/0296327 | A1 * | 10/2016 | Eberhardt | A61F 2/2436 |
| 2017/0172771 | A1 * | 6/2017 | Bruckheimer | A61B 17/12036 |
| 2017/0231765 | A1 * | 8/2017 | Desrosiers | A61F 2/2418 |
| | | | | 623/2.11 |
| 2017/0325948 | A1 * | 11/2017 | Wallace | A61F 2/2409 |
| 2017/0340434 | A1 * | 11/2017 | Cerchiari | A61M 25/1002 |
| 2017/0340460 | A1 * | 11/2017 | Rosen | A61F 2/07 |
| 2018/0206986 | A1 * | 7/2018 | Noe | A61F 2/2412 |
| 2018/0344994 | A1 * | 12/2018 | Karavany | A61M 27/002 |
| 2019/0008628 | A1 | 1/2019 | Eigler et al. | |
| 2019/0110911 | A1 * | 4/2019 | Nae | A61F 2/07 |
| 2019/0175105 | A1 * | 6/2019 | Dlugach | A61F 2/95 |
| 2019/0262118 | A1 * | 8/2019 | Eigler | A61F 2/2487 |
| 2019/0262129 | A1 * | 8/2019 | Cooper | A61F 2/2427 |
| 2020/0229956 | A1 * | 7/2020 | Jackson | A61B 17/12177 |
| 2020/0375721 | A1 * | 12/2020 | Celermajer | A61F 2/88 |
| 2021/0154032 | A1 * | 5/2021 | Welch | A61L 31/041 |
| 2021/0161637 | A1 * | 6/2021 | Eigler | A61F 2/91 |
| 2021/0308433 | A1 * | 10/2021 | Gifford, III | A61M 25/104 |
| 2021/0353300 | A1 * | 11/2021 | Kottenmeier | A61F 2/915 |
| 2022/0175561 | A1 * | 6/2022 | Doyle | A61F 2/95 |
| 2022/0211492 | A1 * | 7/2022 | Pintor | A61F 2/2418 |
| 2022/0346988 | A1 * | 11/2022 | Okereke | A61F 2/915 |
| 2023/0105665 | A1 | 4/2023 | Gifford et al. | |
| 2023/0110800 | A1 * | 4/2023 | Dienno | A61F 2/2415 |
| | | | | 623/2.11 |
| 2023/0118855 | A1 | 4/2023 | Gifford et al. | |
| 2023/0172757 | A1 * | 6/2023 | Willner | A61F 2/958 |
| | | | | 606/109 |
| 2023/0285172 | A1 * | 9/2023 | King | A61F 2/89 |
| 2024/0216135 | A1 * | 7/2024 | Montorfano | A61M 25/0138 |
| 2024/0261101 | A1 * | 8/2024 | Mulligan | A61F 2/2427 |
| 2024/0398420 | A1 * | 12/2024 | Dahan | A61F 2/915 |

FOREIGN PATENT DOCUMENTS

| | | | | |
|---|---|---|---|---|
| CN | 112618121 A * | 4/2021 | | A61F 2/844 |
| DE | 19653719 A1 | 4/1998 | | |
| EP | 3248645 A1 * | 11/2017 | | A61F 2/966 |
| WO | WO-2018131043 A1 * | 7/2018 | | A61F 2/2466 |
| WO | 2020033933 A1 | 2/2020 | | |
| WO | WO-2020254835 A1 * | 12/2020 | | A61F 2/915 |
| WO | 2021195305 A1 | 9/2021 | | |
| WO | 2021195665 A1 | 9/2021 | | |
| WO | WO-2023091938 A1 * | 5/2023 | | A61M 60/216 |
| WO | WO-2023137000 A1 * | 7/2023 | | A61F 2/2418 |

* cited by examiner

1137

1110a

1106

1139

1110b

1106

EXPANDABLE DEVICES AND ASSOCIATED SYSTEMS AND METHODS

CROSS-REFERENCE TO RELATED APPLICATION(S)

The present application is a 371 U.S. national phase application of International Application No. PCT/US2021/070306, filed Mar. 24, 2021, which claims the benefit of priority to U.S. Provisional Patent Application No. 62/993,845, filed Mar. 24, 2020, both of which are incorporated herein by reference in their entireties.

TECHNICAL FIELD

The present technology relates to expandable devices and associated systems and methods. In particular embodiments, the present technology relates to devices for treating body conduits, such as blood vessels and heart valves, and associated systems and methods of use.

BACKGROUND

There are many situations in interventional vascular procedures where there is a need to inflate a balloon in a vessel while maintaining perfusion through that vessel. For example, when delivering a balloon-expandable stent in a coronary artery, it is preferable to maintain blood flow through the artery to avoid ischemic damage to the myocardium perfused by that artery. One device commonly used to maintain blood flow is a perfusion balloon catheter. These catheters typically have a relatively large central guidewire lumen with holes through the catheter sidewall into the lumen just proximal to the balloon. This allows blood to flow through the side holes, into the guidewire lumen, and out the distal end of the catheter to maintain perfusion when the balloon is inflated and occluding the vessel.

However, these perfusion balloons are typically only used in smaller vessels where a relatively small perfusion lumen is sufficient, and the catheter can be made with a perfusion lumen of a fixed size, for example a lumen of less than 2 mm in diameter. In larger vessels such as the aorta, maintaining adequate distal perfusion without a high pressure gradient through the perfusion lumen requires a much larger lumen.

Two common interventional procedures that utilize balloon expansion are (a) balloon valvuloplasty of the aortic valve, and (b) catheter-based delivery of balloon-expandable replacement aortic valves (commonly referred to as "transcatheter aortic valve replacement" or "TAVR"). FIG. 1 shows the delivery of a replacement aortic valve on a conventional balloon catheter. Conventional practice is to inflate the balloon to a large diameter (about 20-30 mm) at a very high pressure, blocking all flow to the systemic circulation. It also prevents any blood from leaving the left ventricle, which can lead to a dangerous acute expansion of the ventricle. In order to prevent this dangerous expansion of the ventricle, a temporary pacing catheter is placed in the heart and the heart is typically paced at a very high rate (~200 beats per minute) which prevents it from filling between heartbeats. Such rapid ventricular pacing may cause myocardial ischemia, malignant arrhythmias, low output, reduced cerebral oxygen saturation, and/or increased procedure time and risk of stroke. To avoid or reduce the likelihood of these dangers, the valvuloplasty or TAVR balloon is typically inflated for less than a minute.

In a typical balloon catheter, the balloon is formed from a single extrusion which is expanded into the desired balloon shape and welded or bonded to the shaft of a catheter. The sidewall of the catheter is cut to create an opening to connect an inflation lumen running through the catheter shaft to the interior of the balloon. In most clinical applications in which a vessel or valve is being dilated, the outer surface of the balloon is rounded (i.e., has a functionally circular cross-sectional shape) so as to apply a relatively even radial force against the apposing tissue. It is difficult to locate a perfusion lumen at the outer circumference of the balloon while maintaining this rounded/circular shape and providing even radially outward force.

An existing approach to the foregoing challenge of creating a large perfusion lumen in larger balloon catheters is the TRUE® Flow Valvuloplasty Perfusion Catheter (C. R. Bard/Becton Dickenson). The TRUE® Flow device has several smaller balloons arranged around the periphery of a central lumen and surrounded by a fiber-based shell. When inflated, the balloons hold the central lumen open. However, this approach limits the effective pressure which can be applied to the circumference of the balloon, even when these smaller balloons are inflated to a higher pressure. More importantly, the use of multiple balloons employs a large amount of material which increases a deflated diameter of the device and makes delivery of the device through a delivery sheath more difficult. This is especially true in the case of a TAVR balloon that has the additional bulk of the prosthetic valve.

Therefore, there remains a need for improved balloons for interventional procedures, especially within the field of interventional cardiology.

SUMMARY

The subject technology is illustrated, for example, according to various aspects described below, including with reference to FIGS. 2A-17B. Various examples of aspects of the subject technology are described as numbered clauses (1, 2, 3, etc.) for convenience. These are provided as examples and do not limit the subject technology.

1. A stent, comprising:
   a first end portion, a second end portion, and a longitudinal axis extending therebetween, the stent having a collapsed configuration for delivery through a delivery device to a treatment site in a body conduit and an expanded configuration; and
   a plurality of spines extending along the longitudinal axis, the spines comprising first spines and second spines, wherein moving the first spines axially relative to the second spines causes circumferentially adjacent spines to move away from one another, thereby increasing a diameter of the stent.

2. A stent, comprising:
   a first end portion, a second end portion, and a longitudinal axis extending therebetween, the stent having a collapsed configuration for delivery through a delivery device to a treatment site in a body conduit and an expanded configuration, wherein the stent has an initial diameter in the collapsed configuration; and
   a plurality of spines extending along the longitudinal axis, each of the spines extending between first and second ends,
   wherein—
      decreasing a longitudinal distance between the first and second end portions of the stent by a first distance in the collapsed configuration causes a diameter of the stent to increase from the initial diameter to a first expanded diameter, wherein a longitudinal distance between the first and second ends of each of the spines remains substantially constant while the longitudinal distance between the first and second end portions of the stent decreases by the first distance;

decreasing the longitudinal distance between the first and second end portions of the stent beyond the first distance causes the diameter of the stent to increase from the first expanded diameter to a second expanded diameter, wherein the longitudinal distance between the first and second ends of the spines decreases while the longitudinal distance between the first and second end portions decreases beyond the first distance.

3. A stent, comprising:

a first end portion, a second end portion, and a longitudinal axis extending therebetween, the stent having a collapsed configuration for delivery through a delivery device to a treatment site in a body conduit and an expanded configuration; and a plurality of spines extending along the longitudinal axis, each of the spines extending between first and second ends, wherein axial compression of the stent in the collapsed configuration by a first distance causes the spines to move radially away from the longitudinal axis without axially compressing the spines, and wherein continued axial compression of the stent beyond the first distance simultaneously axially compresses the spines, thereby increasing the diameter of the stent.

4. The stent of any one of the previous Clauses, further comprising a plurality of struts, each of the struts extending between and connecting circumferentially adjacent spines.

5. The stent of any one of the previous Clauses, the spines comprising first spines and second spines configured to move in opposing axial directions as the stent expands, the stent further comprising a plurality of struts, each of the struts extending between and connecting one of the first spines to one of the second spines.

6. The stent of Clause 5, wherein each of the struts has a first end connected to one of the first spines and a second end connected to one of the second spines, and wherein, when the first spines and the second spines move axially relative to one another, each of the struts angles away from the corresponding one of the first spines and corresponding one of the second spines, thereby pushing the one of the first spines away from the one of the second spines and increasing a radial distance of the first and second spines from the longitudinal axis of the stent.

7. The stent of any one of Clauses 4 to 6, wherein none of the struts connect directly to another strut.

8. The stent of any one of the previous Clauses, wherein the stent comprises:

a first strut region comprising a plurality of first struts, the first strut region extending about a circumference of the stent at a first axial location along the stent, and a second strut region comprising a plurality of second struts, the second strut region extending about a circumference of the stent at a second axial location longitudinally spaced apart from the first axial location, wherein the first struts are shorter than the second struts.

9. The stent of Clause 8, wherein the stent comprises a plurality of first strut regions, and wherein (a) at least one of the first strut regions is positioned between the second strut region and the first end portion of the stent, and (b) at least another one of the first strut regions is positioned between the second strut region and the second end portion of the stent.

10. The stent of Clause 8, wherein the stent comprises a plurality of first strut regions and a plurality of second strut regions, and wherein (a) at least one of the first strut regions is positioned between the second strut regions and the first end portion of the stent, and (b) at least another one of the first strut regions is positioned between the second strut regions and the second end portion of the stent.

11. The stent of Clause 8, wherein the stent comprises a plurality of first strut regions and a plurality of second strut regions, and wherein (a) at least one of the first strut regions is positioned between the second strut regions and the first end portion of the stent, (b) at least another one of the first strut regions is positioned between the second strut regions and the second end portion of the stent, and (c) none of the first strut regions are disposed between two of the second strut regions.

12. The stent of any one of Clauses 8 to 11, wherein the first strut region(s) and the second strut region(s) include a portion of a spine coextensive with the struts within the respective region.

13. The stent of any one of Clauses 8 to 12, wherein each of the first spines and each of the second spines spans both the first strut region(s) and the second strut region(s).

14. The stent of any one of the previous Clauses, the spines comprising first spines and second spines configured to move in opposing axial directions as the stent expands, wherein— each of the first spines has a fixed end proximate the first end portion of the stent and a free end proximate the second end portion, each of the second spines has a fixed end proximate the second end portion of the stent and a free end proximate the first end portion, and the stent comprises:

a first stop at the first end portion, wherein the first stop is configured to prevent axial movement of the free ends of the second spines proximally beyond the first stop, a second stop at the second end portion, wherein the second stop is configured to prevent axial movement of the free ends of the first spines distally beyond the second stop.

15. The stent of Clause 14, wherein, when the stent is axially compressed such that the free ends of the first spines contact the second stop and the free ends of the second spines contact the first stop, additional axial compression of the stent causes the first and second spines to bow outwardly.

16. The stent of any one of the previous Clauses, wherein— each of the first spines has a fixed end portion and a free end portion;

each of the second spines has a fixed end portion and a free end portion, and wherein, when the first and second spines move axially relative to one another, the free end portions of the first spines move closer to the fixed end portions of the second spines, or vice versa, the free end portions of the second spines move closer to the fixed end portions of the first spines, or vice versa.

17. The stent of any one of the previous Clauses, wherein— each of the first spines has a fixed end portion proximate the first end portion of the stent and a free end portion proximate the second end portion;

each of the second spines has a fixed end portion proximate the second end portion and a free end portion proximate the first end portion, and wherein, when the first and second spines move axially relative to one another, the free end portions of the first spines move closer to the second end portion of the stent, or vice versa, the free end portions of the second spines move closer to the first end portion of the stent, or vice versa.

18. The stent of any one of the previous Clauses, wherein the first spines are fixed relative to the first end portion of the stent along an axial dimension.

19. The stent of any one of the previous Clauses, wherein the second spines are fixed relative to the second end portion of the stent along an axial dimension.

20. The stent of any one of the previous Clauses, wherein the first spines are fixed relative to the first end portion of the stent along an axial dimension and the second spines are fixed relative to the second end portion of the stent along the axial dimension.

21. The stent of any one of the previous Clauses, wherein the stent includes a band at the first end portion, wherein the band is continuous with the first spines.

22. The stent of any one of the previous Clauses, wherein the stent includes a band at the first end portion, wherein the first spines are fixed relative to the band.

23. The stent of any one of the previous Clauses, wherein the stent includes a band at the second end portion, wherein the band is continuous with the second spines.

24. The stent of any one of the previous Clauses, wherein the stent includes a band at the second end portion, wherein the second spines are fixed relative to the band.

25. The stent of any one of the previous Clauses, wherein, when the stent is in an expanded configuration, a diameter of the stent tapers in the direction of the first end portion.

26. The stent of any one of the preceding Clauses, wherein, when the stent is in an expanded configuration, a diameter of the stent tapers in the direction of the second end portion.

27. The stent of any one of the preceding Clauses, wherein, when the stent is in an expanded configuration, a diameter of the stent tapers in the direction of the first end portion and in the direction of the second end portion.

28. The stent of any one of the preceding Clauses, wherein the stent has been heat treated to have a preset shape in an intermediate expanded configuration.

29. The stent of any one of the preceding Clauses, wherein the stent has been heat treated to have a preset shape in a fully expanded configuration.

30. The stent of any one of the preceding Clauses, wherein the stent further includes a cover extending over all or a portion of the stent.

31. The stent of any one of the preceding Clauses, wherein the stent is formed of a laser cut sheet of material or a laser cut tube.

32. The stent of any one of the preceding Clauses, wherein the stent is not a braid.

33. The stent of any one of the preceding Clauses, wherein the first and second spines alternate about the circumference of the stent.

34. The stent of any one of the previous Clauses, wherein decreasing a longitudinal distance between the first end portion and the second end portion causes the circumferentially adjacent spines to move away from one another.

35. The stent of any one of the preceding Clauses, wherein the stent is configured to be expanded to exert a radially outward force sufficient to dilate a stenosed native valve and/or an aortic, vascular, or gastrointestinal stricture.

36. The stent of any one of the preceding Clauses, wherein the stent is configured to be expanded to a diameter that is at least one-third of a diameter of the body conduit.

37. The stent of any one of the preceding Clauses, further comprising a valve coupled to the stent, wherein the valve is configured to control fluid flow through the lumen of the stent in the expanded configuration.

38. The stent of Clause 37, wherein the valve is a one-way valve.

39. The stent of Clause 37 or 38, wherein the valve is one of an iris valve, a multi-leaflet valve, a duckbill valve, or a windsock valve.

40. The stent of any one of the preceding Clauses, further comprising an expandable implantable valve apparatus positioned around an outer surface of the stent.

41. The stent of Clause 40, wherein the expandable implantable valve apparatus comprises a stent and a prosthetic heart valve configured for implantation at a native valve annulus.

42. The stent of any one of the preceding Clauses, wherein the body conduit is a blood flow passage.

43. The stent of any one of the preceding Clauses, wherein the body conduit is a native valve annulus.

44. The stent of any one of the preceding Clauses, wherein the body conduit is a native heart valve annulus.

45. The stent of any one of the preceding Clauses, wherein the body conduit is an aortic valve annulus.

46. A device for treating a blood flow passage of a patient, the device comprising:

an expandable device comprising a plurality of spines and a plurality of struts, each of the spines extending between first and second ends, wherein the struts extend between and connect circumferentially adjacent spines, and wherein the expandable device has a first end portion and a second end portion opposite the first end portion along the longitudinal axis of the expandable device;

wherein the expandable device moves from a collapsed configuration to a first expanded configuration when an axial distance between the first and second end portions of the expandable device is decreased while an axial distance between the first and second ends of each of the spines remains substantially constant, wherein the expandable device moves from the first expanded configuration to a second expanded configuration when the axial distance between the first and second end portions of the expandable device is decreased while the axial distance between the first and second ends of each of the spines decreases, and wherein a diameter of the expandable device in the first expanded configuration is less than a diameter of the expandable device in the second expanded configuration.

47. A device for treating a blood flow passage of a patient, the device comprising:

an expandable device having a collapsed configuration and an expanded configuration in which the expandable device defines a lumen therethrough, the expandable device comprising a plurality of spines and a plurality of struts, each of the spines extending between first and second ends, wherein the struts extend between and connect circumferentially adjacent spines, and wherein the expandable device has a first end portion and a second end portion opposite the first end portion along the longitudinal axis of the expandable device;

wherein, when the expandable device is in the collapsed configuration, axial compression of the expandable device causes at least some of the spines to move axially relative to at least some of the other spines, thereby angling the struts out of alignment with the longitudinal axis and increasing an arc length between adjacent spines.

48. The device of Clause 46 or Clause 47, wherein the plurality of spines includes a plurality of first spines and a plurality of second spines, and wherein, when the longitudinal distance between the first end portion and the second end portion is decreased, the first spines move proximally while the second spines move distally, or vice versa.

49. A stent, comprising:
a first end portion, a second end portion, and a longitudinal axis extending therebetween, the stent having a collapsed configuration for delivery through a delivery device to a treatment site in a body conduit and an expanded configuration;
a plurality of first spines and second spines extending along the longitudinal axis, the first and second spines configured to move in opposing axial directions as the stent expands; and
a plurality of struts, each of the struts extending between and connecting one of the first spines to one of the second spines, and wherein, when the first spines and the second spines move axially relative to one another, the struts push circumferentially adjacent first and second spines away from one another, thereby increasing a radial distance of the first and second spines from the longitudinal axis of the stent.

50. A stent, comprising:
a first end portion, a second end portion, and a longitudinal axis extending therebetween, the stent having a collapsed configuration for delivery through a delivery device to a treatment site in a body conduit and an expanded configuration;
a plurality of first spines and second spines extending along the longitudinal axis, the first and second spines configured to move in opposing axial directions as the stent expands; and
a plurality of struts, each of the struts extending between and connecting one of the first spines to one of the second spines, and wherein, when the first spines and the second spines move axially relative to one another, the struts push circumferentially adjacent first and second spines away from one another, thereby increasing a diameter of the stent.

51. A stent, comprising:
a first end portion, a second end portion, and a longitudinal axis extending therebetween, the stent having a collapsed configuration for delivery through a delivery device to a treatment site in a body conduit and an expanded configuration; and
a plurality of spines extending along the longitudinal axis, the spines comprising first spines and second spines, configured to move in opposing axial directions as the stent expands,
a plurality of struts, each of the struts extending between and connecting one of the first spines to one of the second spines, wherein each of the struts has a first end connected to one of the first spines and a second end connected to one of the second spines, and wherein, when the first spines and the second spines move axially relative to one another, each of the struts angles away from the corresponding one of the first spines and corresponding one of the second spines, thereby pushing the one of the first spines away from the one of the second spines and increasing a radial distance of the first and second spines from the longitudinal axis of the stent.

52. A stent, comprising:
a first end portion, a second end portion, and a longitudinal axis extending therebetween, the stent having a collapsed configuration for delivery through a delivery device to a treatment site in a body conduit and an expanded configuration; and
a plurality of spines extending along the longitudinal axis, the spines comprising first spines and second spines, configured to move in opposing axial directions as the stent expands,
a plurality of struts, each of the struts extending between and connecting one of the first spines to one of the second spines, wherein each of the struts has a first end connected to one of the first spines and a second end connected to one of the second spines, and wherein, when the first spines and the second spines move axially relative to one another, each of the struts angles away from the corresponding one of the first spines and corresponding one of the second spines, thereby pushing the one of the first spines away from the one of the second spines and increasing a diameter of the stent.

53. A method for expanding a stent, the stent having a first end portion, a second end portion, and a longitudinal axis extending therebetween, wherein the stent comprises a plurality of spines extending along the longitudinal axis, each of the spines extending between first and second ends, the spines comprising first spines and second spines, the method comprising:
moving the first spines in a first axial direction and the second spines in a second axial direction opposite the first axial direction by decreasing an axial distance between the first and second end portions of the stent, wherein the relative axial movement of the first and second spines causes the spines to move radially away from the longitudinal axis; and
decreasing the axial distance between the first and second end portions of the stent while decreasing the axial distance between the first and second ends of each of the spines, thereby causing the spines to bow and move radially away from the longitudinal axis.

54. A method, comprising:
positioning a stent in a collapsed configuration at a treatment site within a body conduit, the stent having a first end portion, a second end portion, and a longitudinal axis extending therebetween, wherein the stent comprises a plurality of spines extending along the longitudinal axis, the spines comprising first spines and second spines; and
increasing a diameter of the stent by moving the first spines axially relative to the second spines, thereby causing circumferentially adjacent spines to move away from one another.

55. A method, comprising:
positioning a stent in a collapsed configuration at a treatment site within a body conduit, the stent having a first end portion, a second end portion, and a longitudinal axis extending therebetween, wherein the stent comprises a plurality of spines extending along the longitudinal axis, each of the spines extending between first and second ends;
with the stent in the collapsed configuration, decreasing a longitudinal distance between the first and second end portions of the stent by a first distance, thereby causing a diameter of the stent to increase from a diameter in the collapsed configuration to a first expanded diameter, wherein a longitudinal distance between the first and second ends of each of the spines remains substantially constant while the longitudinal distance between the first and second end portions decreases by the first distance; and after decreasing the longitudinal distance between the first and second end portions of the stent by the first distance, further decreasing the longitudinal distance between the first and second end portions of the stent, thereby causing the diameter of the stent to increase from the first expanded diameter to a second expanded diameter, wherein the longitudinal distance between the first and second ends of the spines decreases while the longitudinal distance between the first and second end portions further decreases.

56. The method of any one of the previous Clauses, wherein axially compressing the stent does not axially compress the spines.

57. The method of any one of the previous Clauses, wherein axially compressing the first and second spines causes the first and second spines to bow radially outwardly.

58. The method of any one of the previous Clauses, wherein the stent comprises struts extending between the first spines and the second spines, and wherein axial movement of the first spines relative to the second spines causes the struts to angle out of alignment with the longitudinal axis, thereby pushing the first and second spines away from one another.

59. A method, comprising:

positioning a stent at a treatment site within a blood flow passage, the stent comprising a plurality of spines and a plurality of struts, the spines extending along a longitudinal axis of the stent and the struts extending between and connecting circumferentially adjacent spines, the stent having a first end portion and a second end portion opposite the first end portion along the longitudinal axis of the stent, wherein the spines comprise first spines and second spines; and moving the first and second spines in opposing longitudinal directions, thereby causing the struts to angle away from the spines and push circumferentially adjacent spines away from one another, thereby increasing a radial distance between the spines and the longitudinal axis of the stent.

60. A method, comprising:

positioning a stent at a treatment site within a blood flow passage, the stent comprising a plurality of spines and a plurality of struts, the spines extending along a longitudinal axis of the stent and the struts extending between and connecting circumferentially adjacent spines, the stent having a first end portion and a second end portion opposite the first end portion along the longitudinal axis of the stent; and radially expanding the stent within the body conduit by decreasing a longitudinal distance between the first and second end portions of the stent.

61. The method of Clause 59 or Clause 60, wherein radially expanding the stent includes pulling or pushing the first end portion while holding the second end portion stationary.

62. The method of Clause 59 or Clause 60, wherein radially expanding the stent includes pulling or pushing the second end portion while holding the first end portion stationary.

63. The method of Clause 59 or Clause 60, wherein radially expanding the stent includes pushing the second end portion away from the first end portion while pulling the first end portion away from the second end portion.

64. The method of Clause 59 or Clause 60, wherein radially expanding the stent includes pulling the second end portion away from the first end portion while pushing the first end portion away from the second end portion.

65. The method of any one of the preceding Clauses, wherein radially expanding the stent includes moving at least one of the spines in a first longitudinal direction and moving at least another one of the spines in a second longitudinal direction opposite the first longitudinal direction.

66. The method of any one of the preceding Clauses, wherein the plurality of spines includes a first plurality of spines and a second plurality of spines, and wherein— each of the first plurality of spines have first ends fixed relative to one another at the first end portion of the stent and free second ends disposed between the first ends and the second end portion of the stent, each of the second plurality of spines have first ends fixed relative to one another at the second end portion of the stent and free second ends disposed between the first ends and the first end portion of the stent.

67. The method of Clause 66, wherein the first and second spines alternate about the circumference of the stent.

68. The method of Clause 66 or 67, wherein each of the struts has a first end coupled to one of the first plurality of spines and a second end coupled to one of the second plurality of spines.

69. The method of any one of Clauses 66 to 68, wherein the stent includes a band at the first end portion, wherein the band is continuous with the first spines.

70. The method of any one of the preceding Clauses, wherein the stent comprises:

a first strut region comprising a plurality of first struts extending about a first circumferential region of the stent, and a second strut region comprising a plurality of second struts extending about a second circumferential region of the stent spaced longitudinally apart from the first circumferential region, wherein the first struts are shorter than the second struts.

71. The method of Clause 70, wherein the stent comprises at least two first strut regions, and wherein (a) at least one of the first strut regions is positioned between the second strut region and the first end portion of the stent, and (b) at least another one of the first strut regions is positioned between the second strut region and the second end portion of the stent.

72. The method of any one of the previous Clauses, wherein the stent has been heat treated to have a preset shape in the expanded configuration.

73. The method of any one of the previous Clauses, wherein the expandable device further includes a cover extending over all or a portion of the stent.

74. The method of any one of the previous Clauses, wherein the stent is a laser-cut stent.

75. A system, comprising:

a first elongated member configured to be intravascularly positioned at a treatment site within a body conduit;

second elongated member configured to be intravascularly positioned at the treatment site, wherein the second elongated member is configured to translate and/or rotate relative to the first elongated member; and a stent comprising any of the stents of Clauses 1 to 52, the stent having a first end portion coupled to the first elongated member and a second end portion coupled to the second elongated member.

76. A system, comprising:

a first elongated member configured to be intravascularly positioned at a treatment site within a body conduit;

second elongated member configured to be intravascularly positioned at the treatment site, wherein the second elongated member is configured to translate and/or rotate relative to the first elongated member; and a stent having a collapsed configuration and an expanded configuration in which the stent defines a lumen therethrough, the stent comprising a plurality of spines and a plurality of struts, the spines extending along a longitudinal axis of the stent and the struts extending between and connecting circumferentially adjacent spines, the stent having a first end portion and a second end portion opposite the first end portion along the longitudinal axis of the stent, wherein the first end portion is carried by a distal portion of the first elongated member and the second end portion is carried by a distal portion of the second elongated member, wherein manipulation of the first and/or second elongated members to increase a longitudinal distance between the first end portion and the second end portion causes the stent to radially expand.

77. A stent comprising struts and spines, wherein the stent is expanded by axial compression which delivers radially expansive force by simultaneously axially compressing the spines and circumferentially expanding the struts.

78. The stent of any one of the previous Clauses, wherein the stent is configured to be detached from a delivery system and permanently implanted in a body passage.

79. A device comprising the stent of Clause 79 and one or more valve elements attached to the stent.

80. The device of Clause 80, wherein the device is configured to be implanted in a native heart valve and/or a replacement heart valve.

81. A stent, comprising:

a first end portion, a second end portion, and a longitudinal axis extending therebetween, the stent having a collapsed configuration for delivery through a delivery device to a treatment site in a body conduit and an expanded configuration, wherein the stent has an initial diameter in the collapsed configuration; and a plurality of spines extending along the longitudinal axis, each of the spines extending between first and second ends, wherein— decreasing a longitudinal distance between the first and second end portions of the stent by a first distance in the collapsed configuration causes a diameter of the stent to increase from the initial diameter to a first expanded diameter, wherein a longitudinal distance between the first and second ends of each of the spines decreases by an amount less than the first distance while the longitudinal distance between the first and second end portions decreases by the first distance;

decreasing the longitudinal distance between the first and second end portions of the stent beyond the first distance causes the diameter of the stent to increase from the first expanded diameter to a second expanded diameter, wherein the longitudinal distance between the first and second ends of the spines decreases while the longitudinal distance between the first and second end portions decreases beyond the first distance.

82. A stent, comprising:

a first end portion, a second end portion, and a longitudinal axis extending therebetween, the stent having a collapsed configuration for delivery through a delivery device to a treatment site in a body conduit and an expanded configuration; and a plurality of spines extending along the longitudinal axis, each of the spines extending between first and second ends, wherein axial compression of the stent in the collapsed configuration by a first distance causes the spines to move radially away from the longitudinal axis while axially compressing the spines by an amount less than the first distance, wherein continued axial compression of the stent beyond the first distance simultaneously axially compresses the spines, thereby increasing the diameter of the stent.

83. A method, comprising:

positioning a stent in a collapsed configuration at a treatment site within a body conduit, the stent having a first end portion, a second end portion, and a longitudinal axis extending therebetween, wherein the stent comprises a plurality of spines extending along the longitudinal axis, each of the spines extending between first and second ends;

with the stent in the collapsed configuration, decreasing a longitudinal distance between the first and second end portions of the stent by a first distance, thereby causing a diameter of the stent to increase from a diameter in the collapsed configuration to a first expanded diameter, wherein a longitudinal distance between the first and second ends of each of the spines remains substantially constant while the longitudinal distance between the first and second end portions decreases by the first distance; and after decreasing the longitudinal distance between the first and second end portions of the stent by the first distance, further decreasing the longitudinal distance between the first and second end portions of the stent, thereby causing the diameter of the stent to increase from the first expanded diameter to a second expanded diameter, wherein the longitudinal distance between the first and second ends of the spines decreases while the longitudinal distance between the first and second end portions further decreases, wherein axially compressing the stent results in axially compression of the spines to a lesser extent than the axial compression of the stent.

84. An expandable structure comprising:

a first end portion, a second end portion, and a longitudinal axis extending therebetween, the expandable structure having a collapsed configuration for delivery through a delivery device to a target location in a conduit and an expanded configuration; and a plurality of spines extending along the longitudinal axis, the spines comprising first spines and second spines, wherein moving the first spines axially relative to the second spines causes circumferentially adjacent spines to move away from one another, thereby increasing a diameter of the expandable structure.

85. An expandable structure comprising:

a first end portion, a second end portion, and a longitudinal axis extending therebetween, the expandable structure having a collapsed configuration for delivery through a delivery device to a desired location in a conduit and an expanded configuration, wherein the expandable structure has an initial diameter in the collapsed configuration; and a plurality of spines extending along the longitudinal axis, each of the spines extending between first and second ends, wherein— decreasing a longitudinal distance between the first and second end portions of the expandable structure by a first distance in the collapsed configuration causes a diameter of the expandable structure to increase from the initial diameter to a first expanded diameter, wherein a longitudinal distance between the first and second ends of each of the spines remains substantially constant while the longitudinal distance between the first and second end portions of the expandable structure decreases by the first distance;

decreasing the longitudinal distance between the first and second end portions of the expandable structure beyond the first distance causes the diameter of the expandable structure to increase from the first expanded diameter to a second expanded diameter, wherein the longitudinal distance between the first and second ends of the spines decreases while the longitudinal distance between the first and second end portions of the expandable structure decreases beyond the first distance.

86. A device comprising:

an expandable device comprising a plurality of spines and a plurality of struts, each of the spines extending between first and second ends, wherein the struts extend between and connect circumferentially adjacent spines, and wherein the expandable device has a first end portion and a second end portion opposite the first end portion along the longitudinal axis of the expandable device;

wherein the expandable device moves from a collapsed configuration to a first expanded configuration when an axial distance between the first and second end portions of the expandable device is decreased while an axial distance between the first and second ends of each of the spines decreases by an amount less than the axial distance, wherein the expandable device moves from the first expanded configuration to a second expanded configuration when the axial distance between the first and second end portions of the expandable device is decreased while the axial distance between the first and second ends of each of the spines decreases, and wherein a diameter of the expandable device in the first expanded configuration is less than a diameter of the expandable device in the second expanded configuration.

87. An expandable structure, comprising:

a first end portion, a second end portion, and a longitudinal axis extending therebetween, the expandable structure having a collapsed configuration for delivery through a delivery device to a treatment site in a body conduit and an expanded configuration; and a plurality of spines extending along the longitudinal axis, each of the spines extending between first and second ends, wherein axial compression of the expandable structure in the collapsed configuration by a first distance causes the spines to move radially away from the longitudinal axis without axially compressing the spines, and wherein continued axial compression of the expandable structure beyond the first distance simultaneously axially compresses the spines, thereby increasing the diameter of the expandable structure.

88. A device comprising:

a first expandable structure comprising:

a first end portion, a second end portion, and a longitudinal axis extending therebetween, the expandable structure having a collapsed configuration for delivery through a delivery device to a treatment site in a body conduit and an expanded configuration, and a plurality of spines extending along the longitudinal axis, each of the spines extending between first and second ends, wherein axial compression of the expandable structure in the collapsed configuration by a first distance causes the spines to move radially away from the longitudinal axis without axially compressing the spines, and wherein continued axial compression of the expandable structure beyond the first distance simultaneously axially compresses the spines, thereby increasing the diameter of the expandable structure, and a second expandable structure disposed within the first expandable structure, wherein the second expandable structure comprises:

a first end portion, a second end portion, and a longitudinal axis extending therebetween, the expandable structure having a collapsed configuration for delivery through a delivery device to a treatment site in a body conduit and an expanded configuration, and a plurality of spines extending along the longitudinal axis, each of the spines extending between first and second ends, wherein axial compression of the expandable structure in the collapsed configuration by a first distance causes the spines to move radially away from the longitudinal axis without axially compressing the spines, and wherein continued axial compression of the expandable structure beyond the first distance simultaneously axially compresses the spines, thereby increasing the diameter of the expandable structure.

89. The expandable structure of Clause 88, wherein each of the first and second expandable structures comprise intermediate portions and tapered end portions on either side of the intermediate portion, and wherein the intermediate portion of the first expandable structure is longer than the intermediate portion of the second expandable structure.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

In FIG. 6A, the expandable device is in a collapsed configuration. In FIG. 6B, the expandable device is in an expanded configuration.

DETAILED DESCRIPTION

Figure 1:
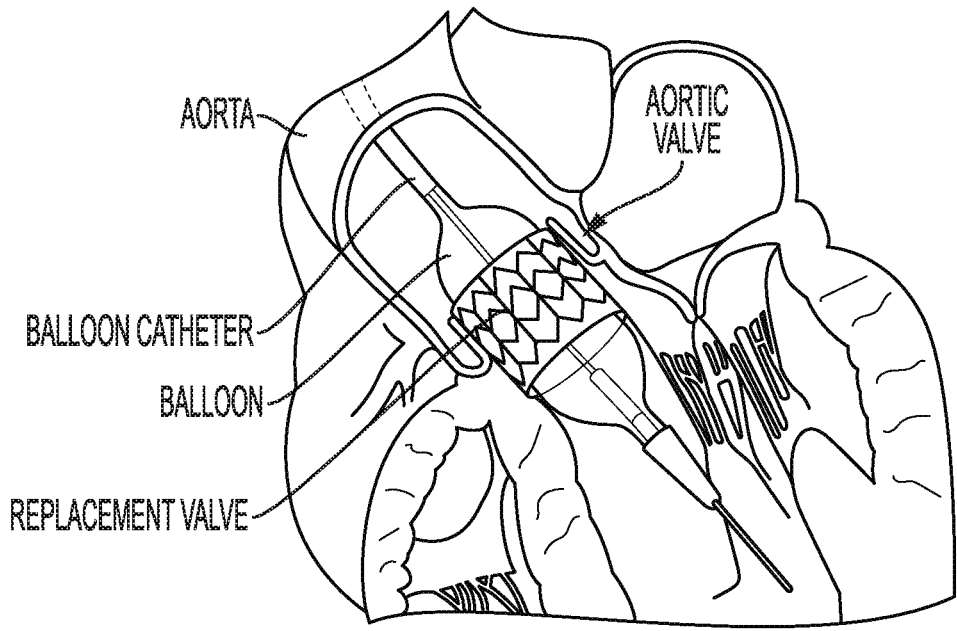
FIG. 1 depicts a conventional balloon catheter and replacement valve positioned at the aortic valve during a typical TAVR procedure.

Specific details of several embodiments of the technology are described below with reference to FIGS. 2A-17B. Although many of the embodiments are described below with respect to devices, systems, and methods for percutaneous replacement of an aortic valve, other applications and other embodiments in addition to those described herein are within the scope of the technology, such as devices, systems, and methods for performing a balloon valvuloplasty, for dilating aortic strictures or other narrowings in the circulatory system, and devices, systems, and methods for percutaneous replacement of a mitral valve, a tricuspid valve, and/or a pulmonic valve. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 2A-17B.

The expandable devices of the present technology include a stent which delivers radially expansive force by simultaneously axially compressing longitudinal spines of the stent and by circumferentially expanding struts of the stent. The geometry of the stents herein enable this dual action, as well as actuation by simple, singular axial compression. The dual action expansion mechanism of the present technology improves the radial expansion force of the stent, making it stronger than a stent which has only axial compression of spines or only circumferential expansion via the struts. The stents of the present technology are also more stable than a stent with only axial compression of spines or circumferential expansion via struts because the combination of axial compression and circumferential expansion reduces the unsupported length of any of the struts or spines, thereby reducing the risk of their deforming and bending. The expandable devices of the present technology provide a very small diameter stent that can deliver a high radially outward force, all while providing an open through-lumen for blood flow. These features make the present technology particularly well suited to the applications of valvuloplasty, stent-valve delivery, dilation of luminal stenoses or strictures, removal of material from body lumens, and other medical applications.

I. Definitions

With regard to the terms "distal" and "proximal" within this description, unless otherwise specified, the terms can reference a relative position of the portions of an interventional device such as a prosthetic valve device and/or an associated delivery device with reference to an operator and/or a location in the vasculature or heart. For example, in referring to a delivery system including the perfusion devices described herein, "proximal" can refer to a position closer to the operator of the device or an incision into the vasculature, and "distal" can refer to a position that is more distant from the operator of the device or further from the incision along the vasculature (e.g., the end of the catheter).

As used herein, "stent" refers to an expandable medical device configured to be inserted into an anatomical vessel or passageway to provide support to the passageway and/or another medical device, and/or to modify biological tissue at the treatment site. "Stent" can also refer to any generally tubular expandable device for any non-medical application.

As used herein, the "collapsed configuration" refers to an unexpanded configuration of the expandable device in which the expandable device is configured to be delivered or withdrawn through a catheter to or from a treatment site. As used herein, the "expanded configuration" refers to a configuration of the expandable device in which the expandable device is partially or fully expanded.

As used herein, the term "longitudinal" refers to a direction along an axis that extends through the lumen of the device while in a tubular configuration, and the term "circumferential" can refer to a direction in a plane that is orthogonal to the longitudinal axis and extends around the circumference of the device when in a tubular configuration.

As used herein, the terms "generally," "substantially," "about," and similar terms are used as terms of approximation and not as terms of degree, and are intended to account for the inherent variations in measured or calculated values that would be recognized by those of ordinary skill in the art.

As used herein, "body conduit" and "blood flow passage" refer to any anatomical structure through which blood or other bodily fluids regularly flow, such as a native annulus (in the heart or anywhere in the vasculature), a heart chamber, a blood vessel, a ureter, an esophagus, a biliary tract, and others.

Figures 2A, 2B:
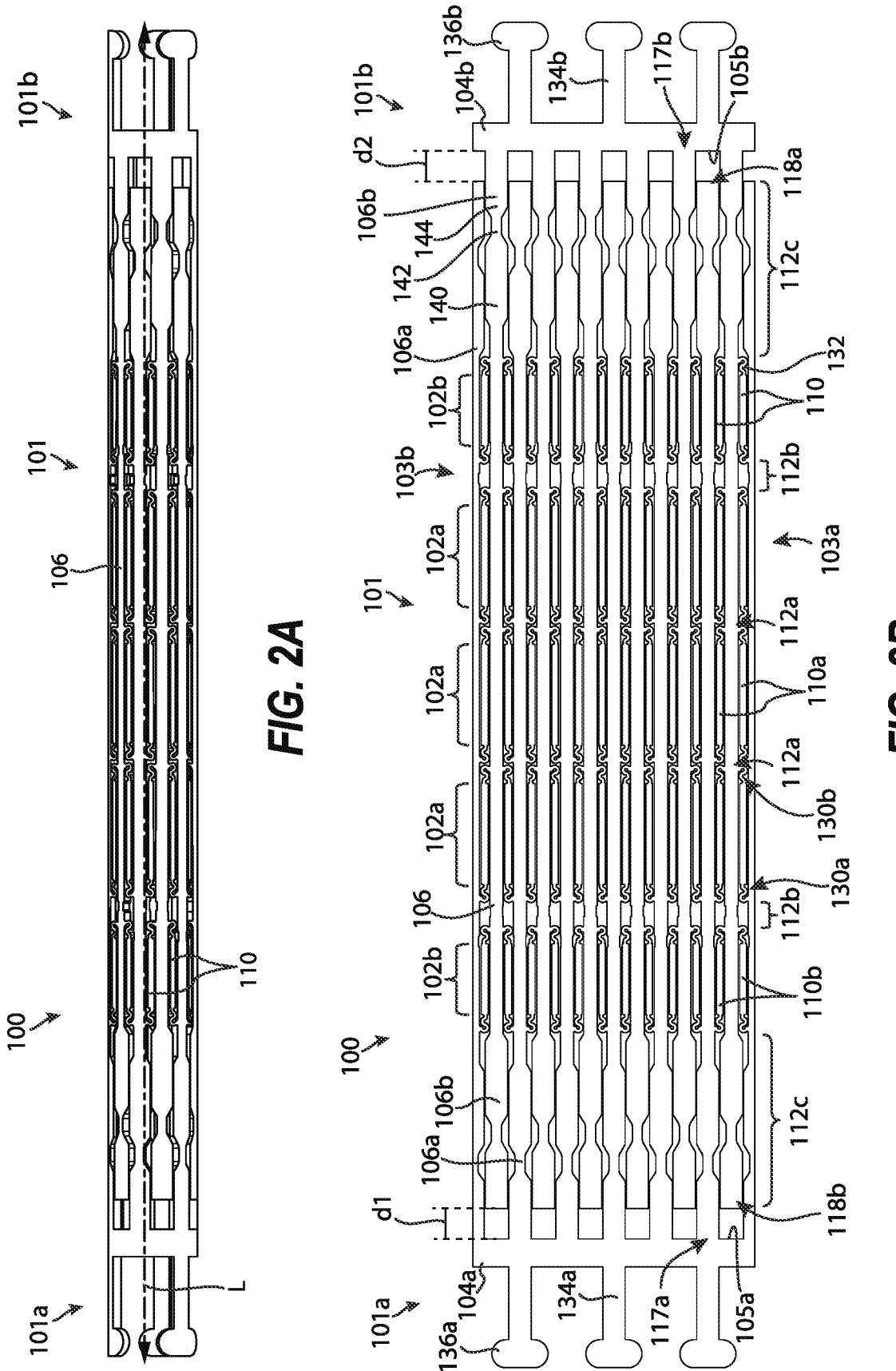
FIG. 2A is a side view of an expandable device of the present technology, shown in a collapsed configuration.
FIG. 2B is a side view of an expandable device of FIG. 2A in a laid-flat configuration.

II. Selected Embodiments of Expandable Devices and Associated Systems and Methods of Use FIG. 2A is an expandable device 100 of the present technology, shown in a collapsed (i.e., unexpanded) tubular configuration. For ease of explanation, FIG. 2B shows the expandable device 100 as it would appear if, while in the collapsed configuration, it was cut longitudinally and then laid flat. When the stent is described in a "laid flat" configuration, it should be assumed that the stent is not under any compressive or tensile forces.

The expandable device 100 is configured to be delivered in the collapsed, tubular configuration to a treatment site within a body conduit, such as a blood flow passage, and radially expanded at the treatment site to treat or facilitate treatment of the body conduit. For example, the expandable device 100 may be configured for expansion within a native valve annulus to widen the native valve opening during a valvuloplasty, or to position a prosthetic valve during a TAVR procedure. Details regarding additional applications of the expandable devices 100 of the present technology are provided herein. Additional applications include non-medical applications in which it may be desirable to expand a tubular structure with a high force while also being able to position the tubular structure at the deployment site in a low-profile configuration.

Referring to FIGS. 2A and 2B, the expandable device 100 may comprise a stent 101 having a first end portion 101a, a second end portion 101b, and a length extending between the first and second end portions 101a, 101b along a longitudinal axis L (labeled in FIG. 2A) of the expandable device 100. The stent 101 can comprise a plurality of longitudinally-extending spines 106 and a plurality of struts 110 extending between circumferentially adjacent spines 106. The struts 110 may be attached to the spines 106 at flexible joints 132. The spines 106 may comprise first spines 106a having fixed ends 117a proximate the first end portion 101a and free ends 118a proximate the second end portion 101b, and second spines 106b having fixed ends 117b proximate the second end portion 101b and free ends 118b proximate the first end portion 101a. The free ends 118a, 118b allow the first and second spines 106a, 106b to slide axially relative to one another when the stent 101 is axially compressed. The relative axial movement of the first and second spines 106a, 106b pushes/pulls the ends of the struts 110 to force the struts 110 to swing out of alignment with the spines 106. In so doing, the struts 110 push circumferentially adjacent spines 106 away from one another, thereby increasing a diameter of the stent 101. As discussed in greater detail below, in some examples the expandable device 100 may be configured to limit the axial movement of the spines 106 such that once the stent 101 has been axially compressed by a certain amount, the spines 106 are prevented from sliding relative to one another and begin to bow or buckle outwardly under the axially compressive forces as well as the circumferentially expansive forces applied by the struts 110.

As previously mentioned, the first and second spines 106a, 106b may have fixed ends and free ends. In some embodiments, for example as shown in FIGS. 2A and 2B, the stent 101 may comprise a first band 104a at the first end portion 101a and a second band 104b at the second end portion 101b. Each of the first and second bands 104a, 104b may comprise a length of the stent 101 along which the stent 101 is circumferentially continuous. The fixed ends 117a of the first spines 106a may be disposed at the first band 104a and the fixed ends 117b of the second spines 106b may be disposed at the second band 104b. As a result, the first band

104a secures the fixed ends 117a of the first spines 106a relative to one another such that axial movement of the first band 104a simultaneously translates the first spines 106a, and the second band 104b secures the fixed ends 117b of the second spines 106b relative to one another such that axial movement of the second band 104b simultaneously translates the second spines 106b.

In some embodiments, the stent 101 does not include the first and/or second bands 104a, 104b and instead the fixed ends 117a of the first spines 106a and/or the fixed ends 117b of the second spines 106b may be fixed relative to one another by other means. For example, in some embodiments the fixed ends 117a, 117b of the first and/or second spines 106a, 106b may be welded, glued, or otherwise fixed to an elongated member (not shown), and/or crimped between a band and an underlying delivery member. In these and other embodiments, the fixed ends 117a, 117b of the first and/or second spines 106a, 106b and/or the free ends 118a, 118b of the first and/or second spines 106a, 106b may comprise eyelets, and a strand of material may be threaded through the eyelets, thereby coupling the fixed ends together. In some embodiments, the strand of material may also be coupled to a delivery member, such as an elongated shaft or push rod.

The first and second spines 106a, 106b may alternate about a circumference of the stent 101 when in the tubular configuration such that no first spine 106a is circumferentially adjacent another first spine 106a and no second spine 106b is circumferentially adjacent another second spine 106b. In some embodiments, two or more first spines 106a may be circumferentially adjacent about the circumference of the stent 101 and/or two or more second spines 106b may be circumferentially adjacent about the circumference of the stent 101. The first spines 106a may have the same length or different lengths, and the second spines 106b may have the same length or different lengths. The first spines 106a and the second spines 106b may have the same length, or the first spines 106a may have a first length and the second spines 106b may have a second length different than the first length.

When the expanded device 100 and/or stent 101 is in the collapsed configuration, the free ends 118a, 118b of the spines 106 may be spaced apart from the corresponding band 104a, 104b by an initial distance d1. As the stent 101 radially expands and the spines 106 move axially relative to one another, the free ends 118a, 118b move closer to the opposing surfaces 105a, 105b of the bands 104a, 104b and, eventually, contact the opposing surfaces 105a, 105b. As detailed herein, contact between the free ends 118a, 118b and the bands 104a, 104b axially compresses the spines 106a, 106b, thereby causing the spines 106 to bow outwardly.

When the expanded device 100 and/or stent 101 is in a collapsed configuration, the free ends 118a of the first spines 106a are spaced apart from the second band 104b by a first distance d1, and the free ends 118b of the second spines 106b are spaced apart from the first band 104a by a second distance d2. The first distance d1 and the second distance d2 may be the same or different when the stent 101 is in the collapsed configuration, and each is measured along a longitudinal dimension of the stent 101. As a distance between the first and second bands 104a, 104b is decreased and the spines 106 move axially relative to one another, the free ends 118a, 118b move closer to opposing surfaces 105a, 105b of the corresponding bands 104a, 104b, and, eventually, contact the opposing surfaces 105a, 105b (at the same time or different times), thereby stopping axial movement of the spine relative to the band. The opposing surfaces 105a, 105b of the bands 104a, 104b, for example, may face in a direction opposite that of the movement of the adjacent free end 118a, 118b such that the free end cannot move along the longitudinal axis L beyond the corresponding opposing surface and/or band. In some embodiments, the axial stop for the free ends may be a portion of the stent 101 other than the bands 104a, 104b, and/or may be a component of the delivery system and/or other portion of the expandable device 100. As detailed elsewhere herein, the interaction between the free ends 118a, 118b and the bands 104a, 104b (or other axial stop) axially compresses the spines 106, thereby causing the spines 106 to bow outwardly.

According to some embodiments, for example as shown in FIGS. 2A and 2B, the end portions of the struts 110 may be coupled to the spines 106 via joints 132. Some or all of the struts 110 may have a first end coupled to one of the spines 106 and a second end coupled to a different one of the spines 106. As such, some or all of the struts 110 may extend between spines 106 and may not directly connect to another strut 110. In some embodiments, some or all of the struts 110 may extend between circumferentially adjacent spines 106 such that the spines 106 and struts 110 alternate about a circumference of the stent 101. In some embodiments, the first end of one, some, or all of the struts 110 is coupled to one of the first spines 106a, and the second end of the strut(s) 110 is coupled to one of the second spines 106b. In some embodiments, the stent may include one or more spines 106 that are not connected to another spine 106 by a strut 110 and/or one or more spines 106 that are not connected to a strut 110.

According to several embodiments, the strut(s) 110 are relatively stiff (as compared to the struts of conventional stents) and substantially straight along their entire lengths. Both of these features provide significant circumferential support to the expanded stent. In contrast, consider a stent having struts disposed between longitudinal spines and configured such that the longitudinal spines do not translate axially relative to one another as the stent expands. For such stents, the struts must be able to substantially deform along their lengths to accommodate the expansion. For example, many conventional stents include chevron-shaped (non-linear) struts that are designed to fold in the middle as the stent expands and contracts. As a result, such stents could not provide nearly as much circumferential strength in its expanded shape as the stents of the present technology. This is true even if such a stent were heat-treated to an expanded shape.

Between the first and second end portions 101a, 101b, the stent 101 may comprise a plurality of strut regions 102 (labeled individually as 102a and 102b) and a plurality of spine regions 112 (labeled individually as 112a, 112b, and 112c), each of which extend about all or a portion of the circumference of the stent 101. The strut regions 102 may include a plurality of struts 110, each separated by one or more spines 106. Some or all of the strut regions 102 can be disposed longitudinally between a pair of spine regions 112, and some or all of the spine regions 112 can be disposed longitudinally between a pair of strut regions 102. In some embodiments, for example as shown in FIGS. 2A and 2B, one or more spine regions 112 are disposed between all of the strut regions 102 and one or both of the first and second end portions 101a, 101b. Some or all of the strut regions 102 can be connected to spine regions 112 on opposing longitudinal sides of the strut region 102. Likewise, some or all of the spine regions 112 can be connected to strut regions 102 on opposing longitudinal sides of the spine region 112.

According to some embodiments, a first longitudinal side of each of the strut regions 102 may be defined by a circumferential band composed of first pairs 130a of joints 132 facing towards the second end portion 101b of the stent 101 (i.e., the struts 110 attached to the joints 132 of the first pairs 130a form a V-shape that opens in the direction of the second end portion 101b), and a second longitudinal side of each of the strut regions 102 may be defined by a circumferential band composed of second pairs 130b of joints 132 facing towards the first end portion 101a of the stent 101 (i.e., the struts 110 attached to the joints 132 of the second pairs 130b form a V-shape that opens in the direction of the first end portion 101a). The first pairs 130a of joints may be disposed along the first spines 106a and the second pairs 130b of joints may be disposed along the second spines 106b.

The strut regions 102 may be longitudinally adjacent one another along the length of the stent 101 such that the band of first pairs 130a of joints 132 of a first one of the strut regions 102 may be longitudinally adjacent the band of second pairs 130b of joints 132 of a longitudinally adjacent second strut region 102.

The spines 106 may extend longitudinally across one, some, or all of the strut regions 102 such that each of the strut regions 102 includes a coextending length of each of the spines 106. In some embodiments, for example as shown in FIGS. 2A and 2B, the struts 110 do not extend longitudinally across any of the spine regions 112 and, as such, spine regions 112 may include only a portion of each spine 106 and do not include any struts 110.

At least when the stent 101 is represented in a laid-flat view, such as in FIG. 2B, one, some, or all of the spines 106 may be generally linear and substantially parallel to (a) the longitudinal axis L, (b) one, some, or all of the struts 110, and/or (c) one, some, or all of the other spines 106. In these and other embodiments, when the stent 101 is in the collapsed configuration, one, some, or all of the spines 106 may be generally linear and substantially parallel to (a) the longitudinal axis L, (b) one, some, or all of the struts 110, and/or (c) one, some, or all of the other spines 106. As the stent begins to expand, portions of the spines 106 will begin to bend as the intermediate regions of the spines 106 move radially away from the longitudinal axis L while the fixed ends 117a, 117b remain radially fixed relative to the longitudinal axis L.

Some or all of the struts 110 may be generally linear along all or a portion of their lengths, as shown in FIGS. 2A and 2B. At least when the stent is represented in a laid-flat view, such as in FIG. 2B, the struts 110 may be generally linear and substantially parallel to (a) the longitudinal axis L, (b) one, some, or all of the spines 106, and/or (c) the other struts 110 within the same strut region 102 and/or some or all of the other strut regions. In these and other embodiments, when the stent 101 is in the collapsed configuration, the struts 110 may be generally linear and substantially parallel to (a) the longitudinal axis L, (b) one, some, or all of the spines 106, and/or (c) the other struts 110 within the same strut region 102 and/or some or all of the other strut regions. The struts 110 may be generally linear and angled relative to the longitudinal axis L and/or angled with respect to one, some, or all of the spines 106 when the stent 101 is in an expanded configuration. In some embodiments, all or a portion of one or more of the struts 110 may be curved when the stent is in a collapsed configuration and/or when the stent 101 is in an expanded configuration. For example, the struts may not have hinges at their ends, and the longitudinal translation of spines may cause the struts to deform into an s-shape, which still circumferentially expands the stent as described herein In some embodiments, struts 110 within different strut regions 102 may have different lengths. For example, the stent 101 may have one or more first strut regions 102*a* with first struts 110*a* having a first length and one or more second strut regions 102*b* with second struts 110*b* having a second length less than the first length. One or more of the first strut region(s) 102*a* may be positioned at a more central region of the stent, and one or more second strut regions 102*b* may be positioned on either side of the first strut region(s) 102*a* such that one or more second strut regions 102*b* (e.g., one, two, three, four, etc.) are between the first strut region(s) 102*a* and the first end portion 101*a* of the stent 101, and at least one second strut region(s) 102*b* is between the first strut region(s) 102*a* and the second end portion 101*b* of the stent 101. When the stent 101 is expanded, the longer first struts 110*a* of the first strut region(s) 102*a* push the circumferentially adjacent spines 106 away from one another to a greater extent than do the shorter struts 110*b* of the second strut region(s) 102*b*, thereby forming tapered portions 150*a*, 150*b* of the stent 100 in the expanded configuration (see, for example, FIG. 7).

In FIGS. 2A and 2B, the stent 101 has three first strut regions 102*a* and two second strut regions 102*b*. In other embodiments, the stent 101 may have more or fewer first strut regions 102*a* (e.g., one first strut region, two first strut regions, four first strut regions, etc.) and/or more or fewer second strut regions 102*b* (e.g., one second strut region, three second strut regions, four second strut regions, etc.). Likewise, the stent 101 may have more than two strut regions having struts of different lengths. For example, the stent 101 may have three, four, five, six, etc. strut regions, each having a different strut length than the other strut regions 102. In some embodiments, the struts 110 of all of the strut regions 102 have substantially the same length. In some embodiments, none of the struts 110 have the same length.

According to some embodiments, for example as shown in FIGS. 2A and 2B, the stent 101 may include spine regions 112 having different lengths. In those embodiments where the spines 106 extend across all of the strut regions 102 and at least two of the strut regions 102 are spaced apart from one another (for example as shown in FIGS. 2A and 2B), the spine region(s) 112 comprise circumferential bands that do not include any struts 110. In the example shown in FIGS. 2A and 2B, the stent includes first spine regions 112*a*, second spine regions 112*b*, and third spine regions 112*c*, each having different lengths. The individual lengths of the first spine regions 112*a* may be less than the individual lengths of the second spine regions 112*b*, and the individual lengths of the second spine regions 112*b* may be less than the individual lengths of the third spine regions 112*c*. In some embodiments, the lengths of the first, second, and/or third spine regions 112*a*, 112*b*, 112*c* may be substantially the same.

As shown in FIGS. 2A and 2B, the first spine regions 112*a* may be positioned between adjacent first strut regions 102*a*, the second spine regions 112*b* may be positioned between the first strut regions 102*a* and the second strut regions 102*b*, and the third spine regions 112*c* may be positioned between the second strut regions 102*b* and the first and second end portions 101*a*, 101*b*. In some embodiments, the first strut regions 102*a* may abut one another such that the joints 132 associated with the first strut regions 102*a* axially abut or overlap one another when the stent is in a collapsed state. In such embodiments, the first spine region 112*a* may not exist or may have a negligible length.

In some embodiments, a width of one, some, or all of the spines 106 may vary along the length of the respective spine 106. For example, one, some, or all of the spines 106 may have a first width along the portion(s) of the spine 106 coextensive with the strut regions 102, and a second width along the portion(s) of the spine 106 outside of the strut regions 102. The second width may be greater or less than the first width. The portions of the first and second spines 106*a*, 106*b* between the strut regions 102 and the end portions 101*a*, 101*b* (for example, within the third spine region 112*c*) may have greater average widths than the portions of the first and second spines 106*a*, 106*b* spanning the strut regions 102. Along the third spine region 112*c*, the first and second spines 106*a*, 106*b* may have first and second wide portions 140, 144 separated by a narrowed portion 142 (only labeled on a single second spine 106*b* for ease of illustration). In some embodiments, the stent 101 may be configured to preferentially bend at the narrowed portion 142 as the stent 101 expands. The first and second wide portions 140, 144 may have a width that is greater than a width of a portion of the corresponding first or second spine 106*a*, 106*b* coextensive with the strut regions 102. It may be beneficial for one or more of the spines 106 to have a greater width nearer the end portions and/or along a length of the stent 101 devoid of strut regions 102 to provide greater structural support to the stent 101 once expanded.

In some embodiments, a width of one, some, or all of the spines 106 is substantially constant along the third spine regions 112*c* and does not include a narrowed portion 142. In some embodiments, a width of one, some, or all of the spines 106 is constant along the entire length of the spine 106.

In FIGS. 2A and 2B, the stent 101 has two first spine regions 112*a*, two second spine regions 112*b*, and two third spine regions 112*c*. In other embodiments, the stent 101 may have more or fewer first spine regions 112*a* (e.g., no first spine regions, one first spine region, three first spine regions, four first spine regions, etc.), more or fewer second spine regions 112*b* (e.g., no second spine regions, one second spine region, three second spine regions, four second spine regions, etc.), and/or more or fewer third spine regions 112*c* (e.g., no third spine regions, one third spine region, three third spine regions, four third spine regions, etc.). Additionally or alternatively, the stent 101 may have more or fewer than three spine regions 112 having different lengths. For example, the stent 101 may have three, four, five, six, etc. spine regions, each having a different length than the other spine regions 112. In some embodiments, all of the spine regions 112 of the stent 101 have substantially the same length. In some embodiments, none of the spine regions 112 have the same length.

Figure 3:
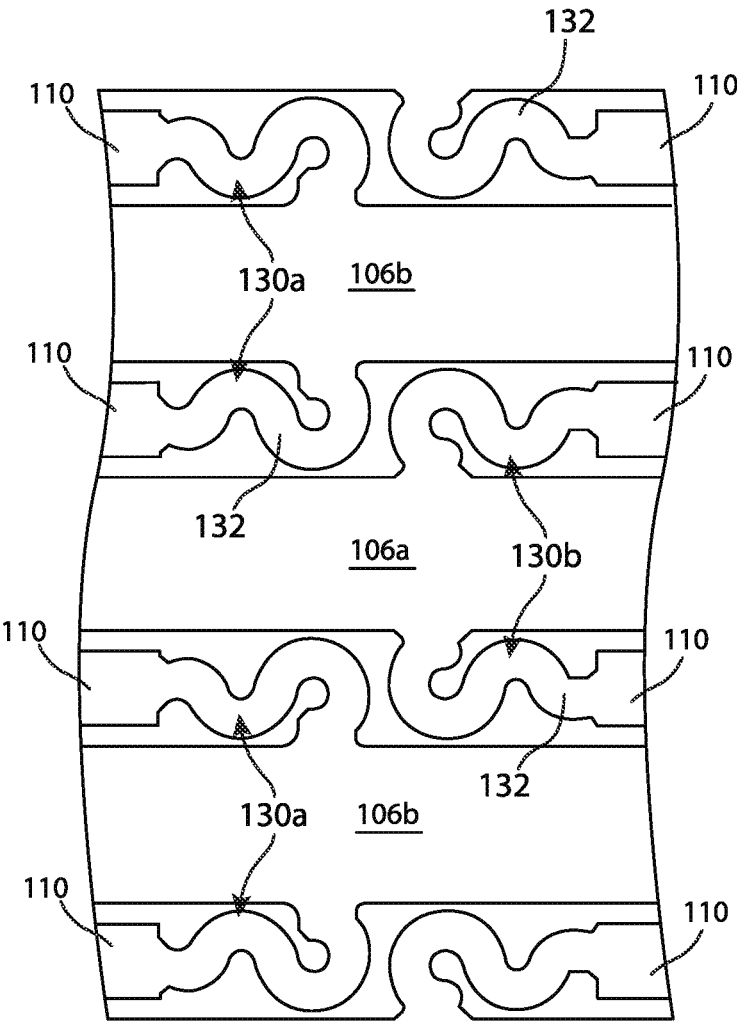
FIG. 3 is an enlarged view of a portion of the expandable device shown in FIGS. 2A and 2B.

FIG. 3 shows an enlarged view of a portion of the stent 101 showing several joints 132. As shown, the stent 101 may include first pairs of joints 130*a* between the first spines 106*a* and the struts 110 connected thereto and second pairs of joints 130*b* between the second spines 106*b* and the struts 110 connected thereto. The first pairs of joints 130*a* may face towards the free ends 118*a* of the first spines 106*a* and/or the second end portion 101*b* of the stent 101, and the second pairs of joints 130*b* may face towards the free ends 118*b* of the second spines 106*b* and/or the first end portion 101*a* of the stent 101. As the stent 101 moves from the collapsed configuration to the expanded configuration, the struts 110 at the first pairs of joints 130*a* may form a chevron or V-shape that opens towards the second end portion 101*b*, and the struts 110 at the second pairs of joints 130*b* may form a chevron or V-shape that opens towards the first end portion 101*a*.

The joints 132 may coincide with the first and second end portions of the struts 110, or may extend from the first and second end portions of the struts 110. The joints 132 can have a width, thickness, and shape designed to allow the struts 110 to swing away from the adjacent spines 106 as the expandable device 100 and/or stent 101 radially expands, as well as to withstand the forces exerted on the struts 110 by the spines 106 as the ends of the spines 106 and/or stent 101 is axially compressed and as the stent is subjected to radial compressive forces.

Figure 4:
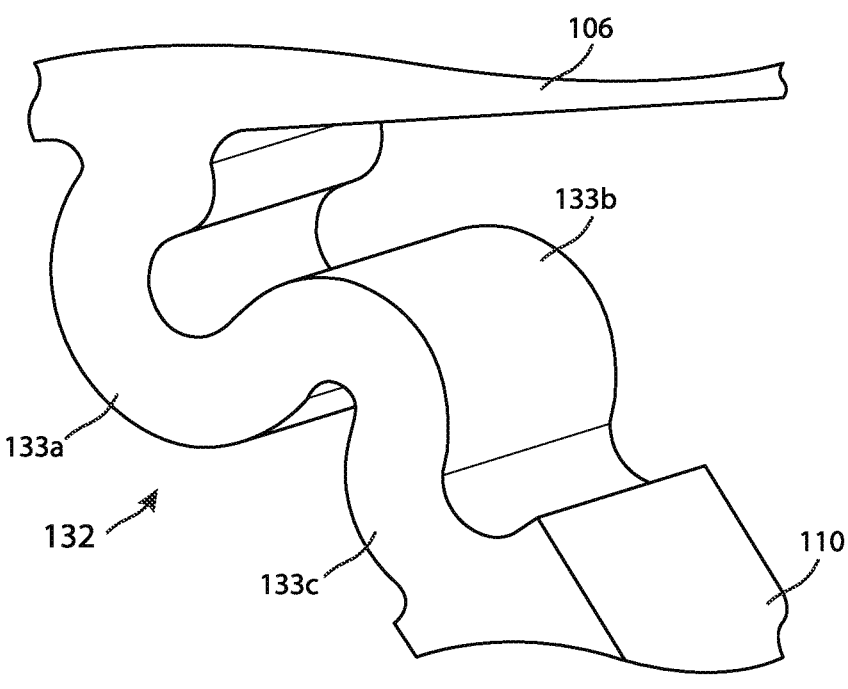
FIGS. 4 and 5 are example joints configured in accordance with the present technology.
Figure 5:
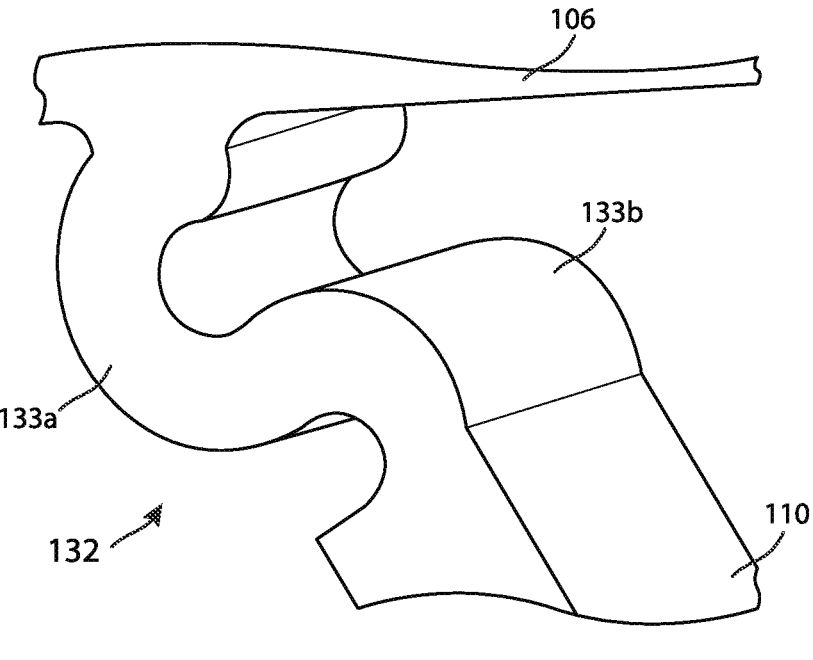

The length, width, thickness, and/or geometry of each of the joints 132 may be varied depending on the length of the strut 110 to which the joint 132 is attached or the angle through which the strut swings as the stent is expanded, as discussed in greater detail herein. One, some, or all of the individual joints 132 may have a non-linear shape, such as a c-shape, an s-shape, a serpentine shape, a sinusoidal shape, a zig-zag shape, and/or any segment with one or more inflection points when the stent is in a collapsed configuration. In some embodiments, none, some, or all of the individual joints 132 have the same shape. In some embodiments, none, some, or all of the individual joints 132 have different shapes. FIGS. 4 and 5, for example, show two different joints 132 configured for use with the expandable devices 100 of the present technology. As shown in FIG. 4, one, some, or all of the joints 132 may have three turns (individually labeled 133*a*, 133*b*, and 133*c*). As shown in FIG. 5, one, some, or all of the joints 132 may have two turns (individually labeled 133*a*, 133*b*). In some embodiments, one, some, or all of the joints 132 may have a single turn. It may be beneficial to incorporate more turns in a given joint 132 the greater the range of flexion the joint is expected to experience 132 during expansion and collapse of the stent 101 and/or once positioned in a body conduit. The width, thickness, or curvature of any given turn or turns may be adjusted to target stress at desired locations in order to increase hinge deflection at said locations. Moreover, the width, thickness, or curvature of any given turn or turns may be adjusted to more evenly distribute stress, such as in order to limit or reduce high-stress spots and likely subsequent hinge breaks.

The expandable device 100 may optionally include one or more connecting portions configured to couple the expandable device 100 to a delivery device (such as, for example so that a physician may manipulate an extracorporeally positioned proximal portion of the delivery device to translate and/or rotate the corresponding end portion 101*a*, 101*b*, or so that the corresponding end portion 101*a*, 101*b* is held stationary (i.e., cannot translate or rotate) relative to the delivery device. The stent 101 may include, for example, a coupler at its first end portion 101*a* configured to non-detachably engage the distal end portion of a delivery element (either directly or through another coupling means), and/or a second coupler at its second end portion 101*b* configured to non-detachably engage the distal end portion of a delivery element (either directly or through another coupling means).

The connecting portions may comprise one or more protrusions, projections, tabs, threaded shafts, threaded rods, hooked extensions, eyelets, or other coupling means. According to some embodiments, for example as shown in FIGS. 2A and 2B, the connecting portion may comprise one or more projections. For example, the stent 101 may include first projections 134*a* continuous with and projecting proximally from the first band 104*a*, and one or more second projections 134*b* continuous with and projecting distally from the second band 104*b*. One, some, or all of the first and/or second projections 134*a*, 134*b* may optionally include a tab 136*a*, 136*b* extending laterally away from the corresponding first or second projection 134*a*, 134*b*. As discussed in greater detail below with reference to FIGS. 9A and 9B, the projections 134 may be configured to mate with a complementary portion of a connector associated with an elongated delivery member, or the projections 134 may be configured to mate directly with the distal portion of an elongated delivery member. In some embodiments, only the first end portion 101*a* of stent has projections, and in some embodiments only the second end portion 101*b* has projections. According to some embodiments, the stent 101 does not include any projections and/or connecting portions.

To transform the expandable device 100 from the collapsed configuration to an expanded configuration, the stent 101 may be axially compressed such that an axial distance between the first and second end portions 101*a*, 101*b* is decreased. For example, to axially compress the stent 101, the first end portion 101*a* may be held stationary while the second end portion 101*b* is pulled towards the first end portion 101*a*. In some embodiments, the second end portion 101*b* is held stationary while the first end portion 101*a* is pushed towards the second end portion 101*b*. In some embodiments, the first and second end portions 101*a*, 101*b* are pushed/pulled toward one another at the same time.

Figure 6A:
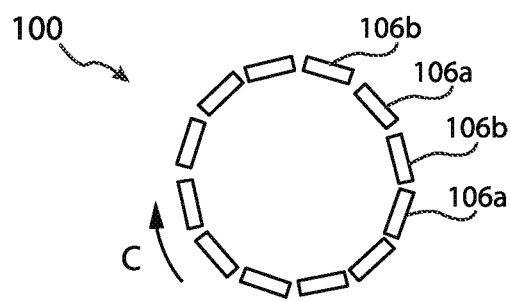
FIGS. 6A and 6B are cross-sectional end views taken along a spine region of an expandable device configured in accordance with the present technology.
Figure 6B:
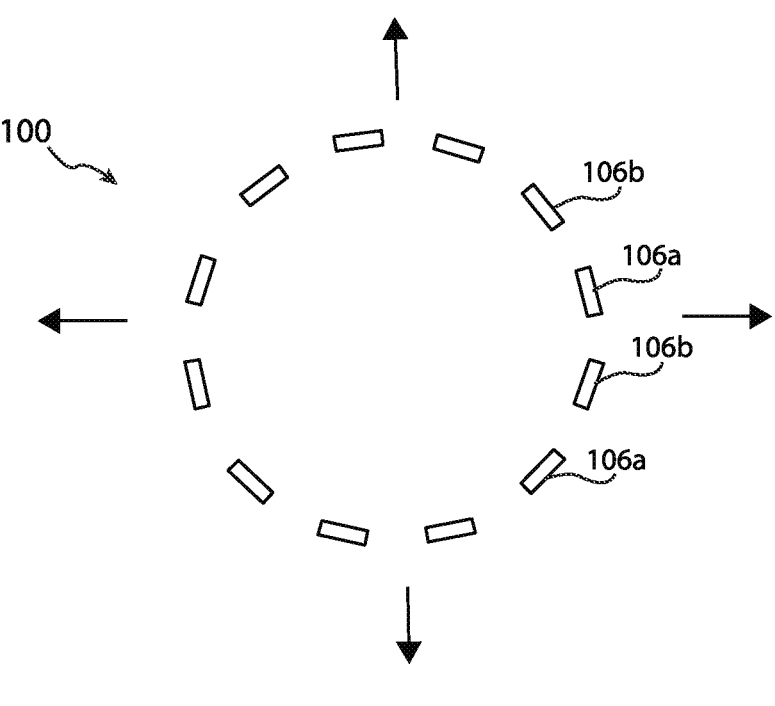

In any case, when the stent 101 is in the collapsed configuration, translation of the first and second end portions 101*a*, 101*b* towards one another moves the first and second spines 106*a*, 106*b* in opposite directions along the longitudinal axis such that the free ends 118*b* of the second spines 106*b* move in the direction of the first end portion 101*a* (or first band 104*a*) and the free ends 118*a* of the first spines 106*a* move in the direction of the second end portion 101*b* (or second band 104*b*). The opposing motion of adjacent spines 106 flexes the joints 132 and forces the struts 110 to angle away from the spines 106 to which they are connected. The angling struts 110 push circumferentially adjacent first and second spines 106*a*, 106*b* away from one another, thereby increasing a diameter of the stent 101. FIGS. 6A and 6B, for example, are cross-sectional axial views showing the first and second spines 106*a*, 106*b* as the stent moves from a collapsed configuration (FIG. 6A) towards an expanded configuration (FIG. 6B). As shown, in the expanded configuration, the arc length between circumferentially adjacent spines 106*a*, 106*b* increases as the stent 101 radially expands.

After the stent 101 has been axially compressed a certain distance (such as the first distance d1 or the second distance d2), the free ends 118*a*, 118*b* of the first and second spines 106*a*, 106*b* contact the first and second bands 104*a*, 104*b*, respectively. Before this contact, radial expansion of the stent 101 was driven by the angling struts 110 pushing circumferentially adjacent spines 106 away from one another. While the stent 101 as a whole was axially compressed during that time (or at least an axial distance between the first and second end portions 101*a*, 101*b* decreased), the spines 106 were free to slide axially and thus were not subject to axial compression, or at least a longitudinal distance between the first and second ends of each of the spines decreased by an amount less than a longitudinal distance between the first and second end portions of the stent was decreased. Once the free ends 118*a*, 118*b* of the spines 106 contact the opposing surfaces 105*a*, 105*b* of the bands 104*a*, 10*b*, respectively, the spines 106 can no longer slide axially relative to one another, and continued axial compression of the stent 101 causes axial compression of the spines 106. As a result, the spines 106 bow outwardly due to axial compression as well as due to the swinging open of the struts 110. Thus, radial expansion of the stent 101 occurs in two phases. During the first phase, the sliding spines 106 and angling struts 110 cause the stent 101 to radially expand, and during the second phase, axial compression of the spines 106 and the resulting buckling of the spines 106 also causes the stent 101 to radially expand.

Accordingly, when the stent 101 is in an expanded configuration (partial or full), (a) the free ends 118a of the first spines 106a are either spaced apart from the second band 104b by a distance that is less than the first distance d1 in the collapsed configuration, or in contact with an opposing surface 105a of the first band 104a, and (b) the free ends 118b of the second spines 106b are either spaced apart from the first band 104a by a distance that is less than the second distance d2 in the collapsed configuration, or in contact with an opposing surface 105b of the second band 104b.

The first and/or second distances d1, d2 (or "spine travel distance") and the length of the struts 110 may be selected to complement one another to achieve a desired shape and/or diameter in the expanded configuration, and also to ensure the struts 110 do not angle away from the spines 106 beyond a predetermined threshold angle. If the spine travel distance is too long relative to the length of the struts 110, then the struts 110 may extend at an angle relative to the spines 106 greater than the joints 132 can handle, potentially causing the joints 132 to break or otherwise fail. If the angle between the struts 110 and the spines 106 in the expanded configuration is too great, the struts 110 may "lock out," making it very difficult, if not impossible, to collapse the stent 101.

Figure 7:
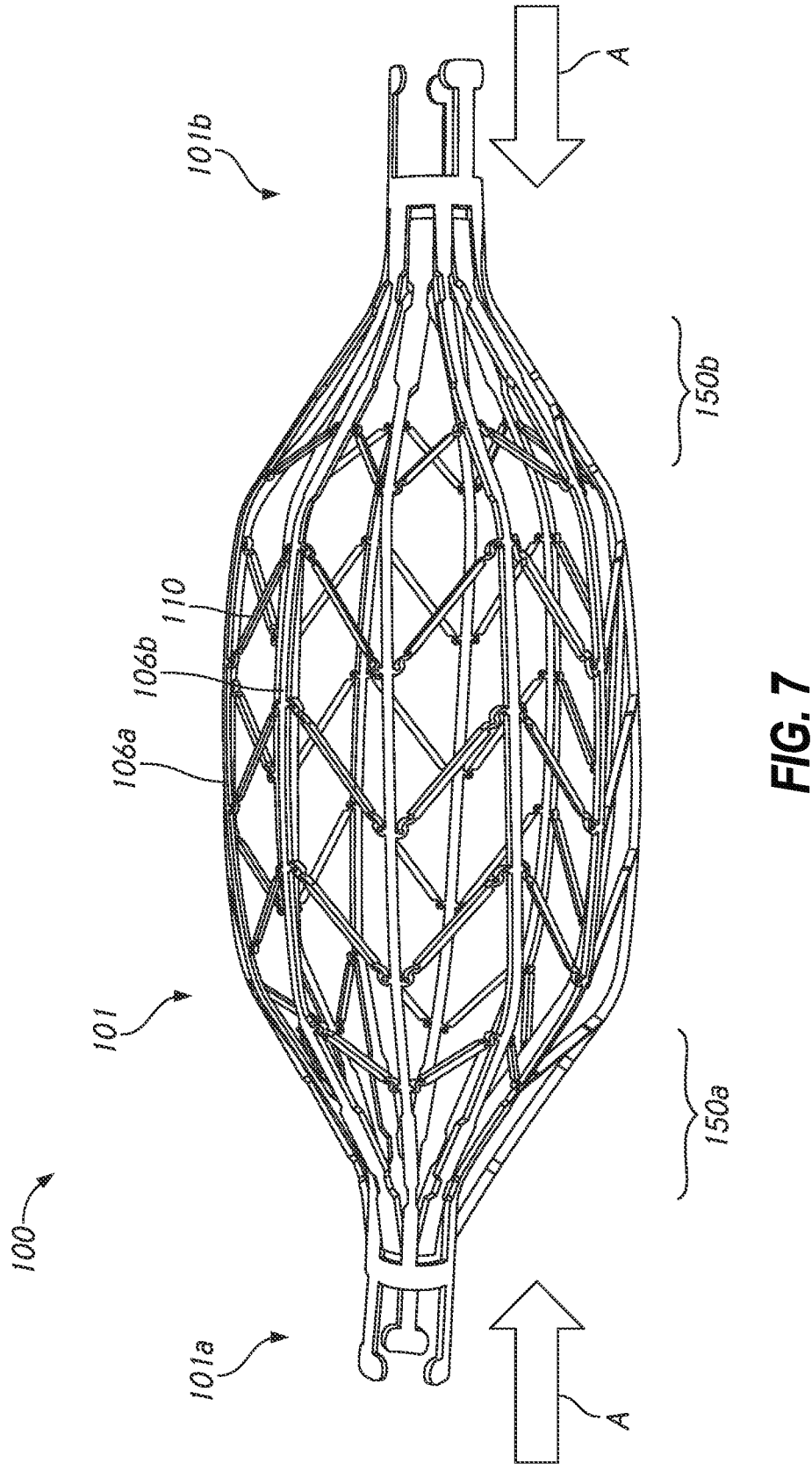
FIG. 7 is a side view of the expandable device shown in FIGS. 2A and 2B in an expanded configuration.

FIG. 7 is a side view of the expandable device 100 in an expanded configuration. As shown in FIG. 7, when the stent is in the expanded configuration, the struts 110 may be positioned at an angle relative to their connected spines 106. For example, in some embodiments the struts 110 form a zig-zag pattern about the circumference of the stent 101, where each of the struts 110 comes together with another strut 110 at a spine 106. The struts 110 may make other patterns about the circumference of the stent 101.

According to some embodiments, for example as shown in FIG. 7, the stent 101 may have tapered end portions 150a, 150b and a generally constant diameter along an intermediate portion of its length. The portion of the stent 101 corresponding to the first strut regions 102a may have a generally cylindrical shape, while a length of the stent 101 corresponding to each of the second strut regions 102b may taper in diameter in the direction of the adjacent end portion. The stent 101 may have other suitable shapes in the expanded configuration. For example, in some embodiments the expandable device 100 may have a generally cylindrical configuration along its entire length in the expanded configuration.

The expanded diameter of the stent 101 may be tailored to the anatomy of the treatment site and its use. When used for the repair or replacement of a heart valve, for example, the expanded diameter of the stent 101 may be selected to avoid acute ventricular overexpansion and provide meaningful blood flow to the systemic circulation. In such embodiments, the expanded diameter of the expandable device 100 and/or stent 101 may have a cross-sectional area of at least about 0.5 cm$^2$ to about 0.8 cm$^2$ and/or at least one-third of a diameter of the native annulus to provide adequate blood flow if combined with another expandable element. If the stent is expanding the heart valve or replacement stent-valve directly, the stent 101 may have an expanded diameter of about 10 mm to about 40 mm, about 20 mm to about 30 mm, greater than about 20 mm, greater than about 25 mm, or greater than about 30 mm. The expandable device 100 may have an expanded diameter of about 10 mm to about 40 mm, about 20 mm to about 30 mm, greater than about 20 mm, greater than about 25 mm, or greater than about 30 mm. In some embodiments, the expandable device 100 and/or stent 101 has a variable diameter over its length. For example, the expandable device 100 and/or stent 101 may have a slightly smaller diameter along a middle region of the device 100 and/or stent 101 to help keep the device 100 and/or stent 101 centered on the valve or other narrowing which is being expanded.

To collapse the stent 101 from the expanded configuration to the collapsed configuration, the stent 101 can be placed under axial tension such that the distance between the first and second end portions 101a, 101b increases.

In some embodiments, the expandable device 100 may optionally include annular restraints 216a, 216b (best shown in FIG. 13) at the first end portion 101a and the second end portion 101b of the stent 101 that extend over at least the free ends 118a, 118b when the stent 101 is in both the collapsed configuration and the expanded configuration. In some embodiments, the expandable device 100 includes an annular constraint 216a at the first end portion 101a (and not at the second end portion 101b), or the expandable device 100 includes an annular constraint 216b at the second end portion 101b (and not at the first end portion 101a). According to some embodiments, the expandable device 100 may comprise more than one annular constraint at the first end portion 101a, more than one annular constraint at the second end portion 101b, or more than one annular constraint at each of the first and second end portions 101a, 101b. The annular constraints 216a, 216b may additionally extend over the additional portions of the stent on either side of the free ends 118a, 118b. For example, the annular constraints 216a, 216b may extend over the fixed ends 117a, 117b, all or a portion of the first and second bands 104a, 104b (if included), and/or all or a portion of the connecting portion (if included). In these and other embodiments, one or both of the annular constraints 216a, 216b may be coupled to a portion of a delivery system, such as one or more components of the delivery system 200, which is described in greater detail below with reference to FIGS. 8-9C.

The annular restraints 216a, 216b radially constrain the free ends 118a, 118b but allow axial movement of the free ends 118a, 118b as the stent is expanded and collapsed. This way, the annular restraints 216a, 216b prevent the free ends 118a, 118b from lifting radially away from the cylindrical surface defined by the first and second bands 104a, 104b and/or fixed ends 117a, 117b when the first and second spines 106a, 106b move axially. As discussed elsewhere herein, the first and second bands 104a, 104b and/or another portion of the stent provide a surface 105 that opposes axial movement of the free ends 118a, 118b and provides the equal and opposite force necessary to compress the spines 106 and cause them to bow outwardly. In some embodiments, such as that shown in FIGS. 2A and 2B, the annular constraints 216a, 216b guide the axial movement of the free ends 118a, 118b into contact with the surfaces 105a, 105b (or other axial stop).

The expandable devices and/or stents of the present technology provide several advantages over the balloon-expandable systems of the prior art. Unlike balloons, the expandable device 100 does not fully occlude the conduit in which it is expanded and thus can remain expanded at the treatment site for an extended period of time (e.g., a minute or more). As a result, the expandable devices of the present technology can provide more effective dilation of a stenosed native valve or expansion of a prosthetic stent-valve, thereby reducing the likelihood of perivalvular leakage or stent slippage. In the case of stent-valve delivery, the extended expansion time also reduces the possibility of incomplete or non-circular stent expansion, which can lead to valve leakage and/or increased valve deterioration and early valve failure. Additionally, the expandable devices of the present technology enable the clinician to dilate the stent-valve more slowly or leave the stent-valve partially dilated for a period of time, which improves the final positioning of the stent-valve as it improves targeting of position and depth of the valve deployment.

Figure 8:
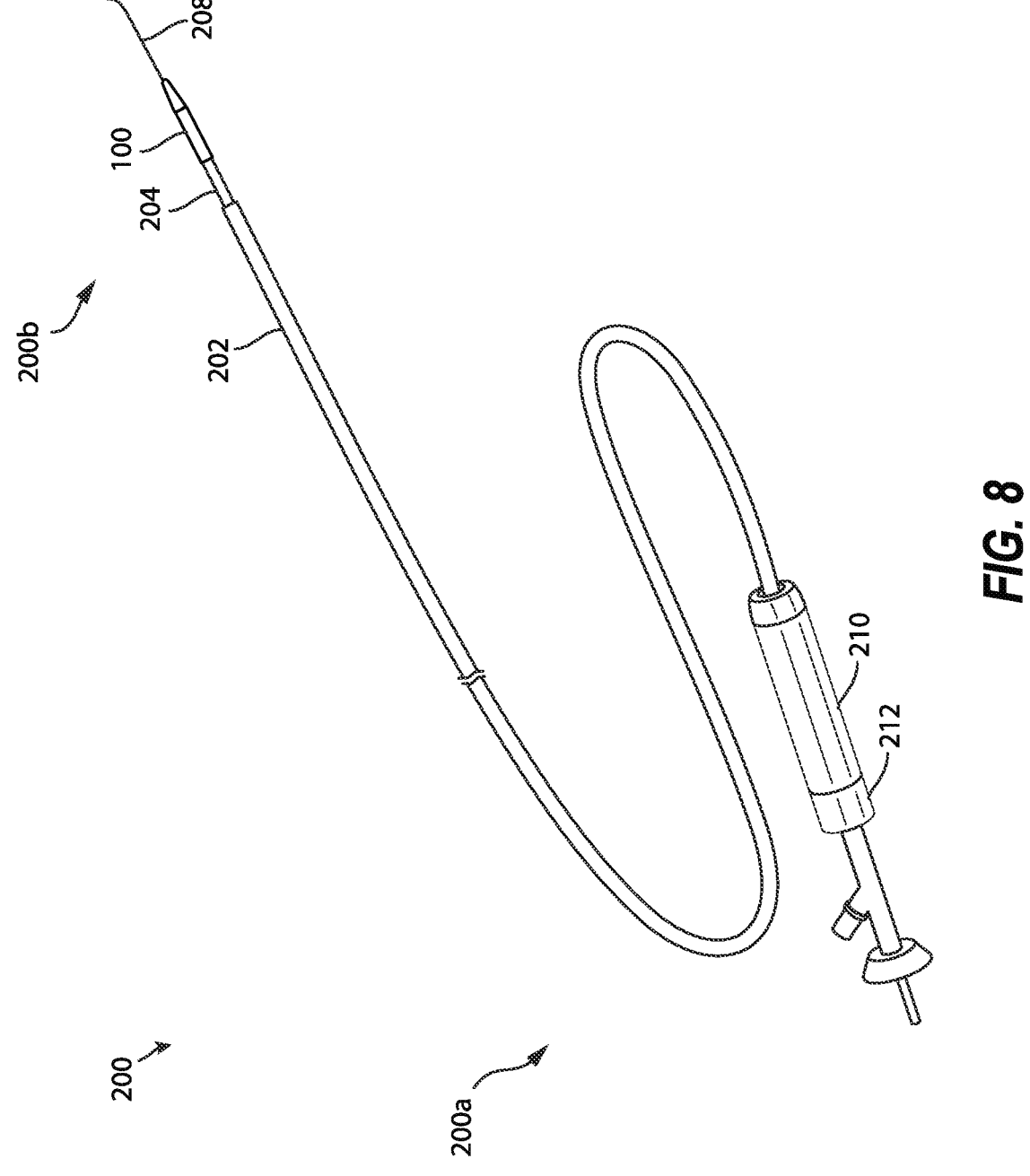
FIG. 8 is a system configured to deliver and deploy an expandable device in accordance with embodiments of the present technology.

FIG. 8 shows an example delivery device 200 configured to position and deploy the expandable device 100 at a treatment site within a body conduit, such as a blood flow passage. The delivery device 200 may have a proximal portion 200a configured to be extracorporeally positioned during delivery of the expandable device 100, and a distal portion 200b configured to be intravascularly positioned within the body conduit proximate the treatment site.

The delivery device 200 includes the expandable device 100 (shown schematically) at the distal portion 200b, a handle 210 at the proximal portion 200a, and a plurality of elongated shafts or members extending therebetween. In some embodiments, for example as shown in FIG. 8, the delivery device 200 includes a first elongated member 202 and a second elongated member 204 configured to be slidably disposed within a lumen of the first elongated member 202, and a third elongated member 206 (see FIG. 9B) configured to be slidably disposed within a lumen of the second elongated member 204. In some embodiments, the delivery device 200 includes more or fewer elongated members and/or lumens than the first, second, and third elongated members 202, 204, 206 (and corresponding lumens).

Figure 9A:
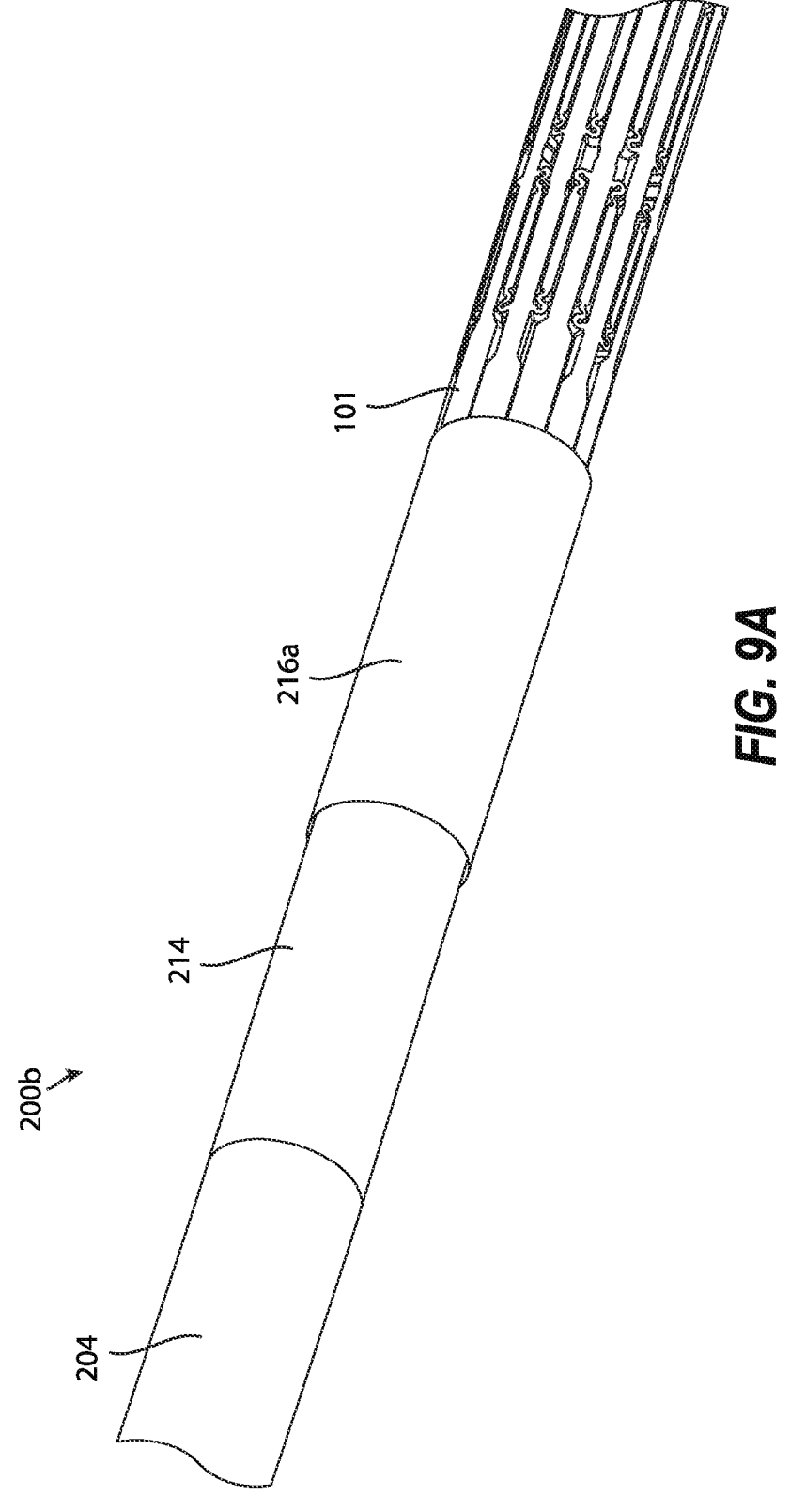
FIGS. 9A-9C are isometric views of a portion of an example delivery system in accordance with the present technology.
Figure 9B:
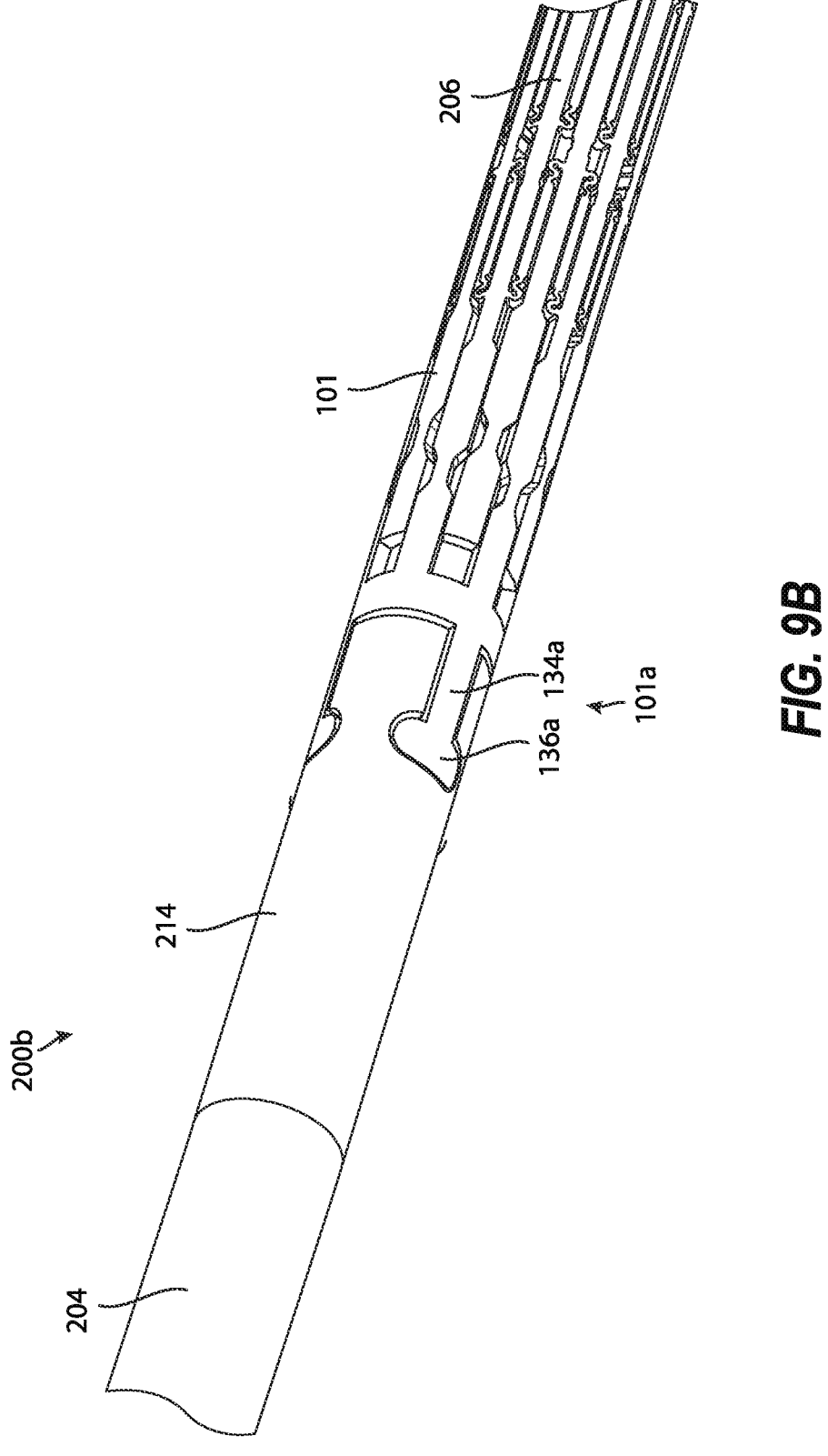

Each of the first, second, and third elongated members 202, 204, 206 may have a proximal end region coupled to the handle 210 and a distal end region at the distal portion of the device 200. FIGS. 9A and 9B are enlarged views of a distal portion 200b of the delivery device 200, shown with and without the annular constraint 216a visible, respectively. As shown, a distal end region of the second elongated member 204 may be fixedly coupled to the first end portion 101a of the expandable device 100 such that the first end portion 101a of the expandable device 100 may be manipulated (e.g., translated and/or rotated) via manipulation of the second elongated member 204 at the handle 210. In some embodiments, for example as shown in FIG. 9A, the distal region of the second elongated member 204 may be coupled to the expandable device 100 indirectly via a connector 214 that mates with the connecting portion (e.g., projection 134a) at the first end portion 101a of the stent. The second elongated member 204 may be fixedly coupled to the connector 214 via an end weld, adhesive, crimped band, and other attachment means. In some embodiments, the distal region of the second elongated member 204 may directly couple to the expandable device 100 and/or stent 101.

Figure 9C:
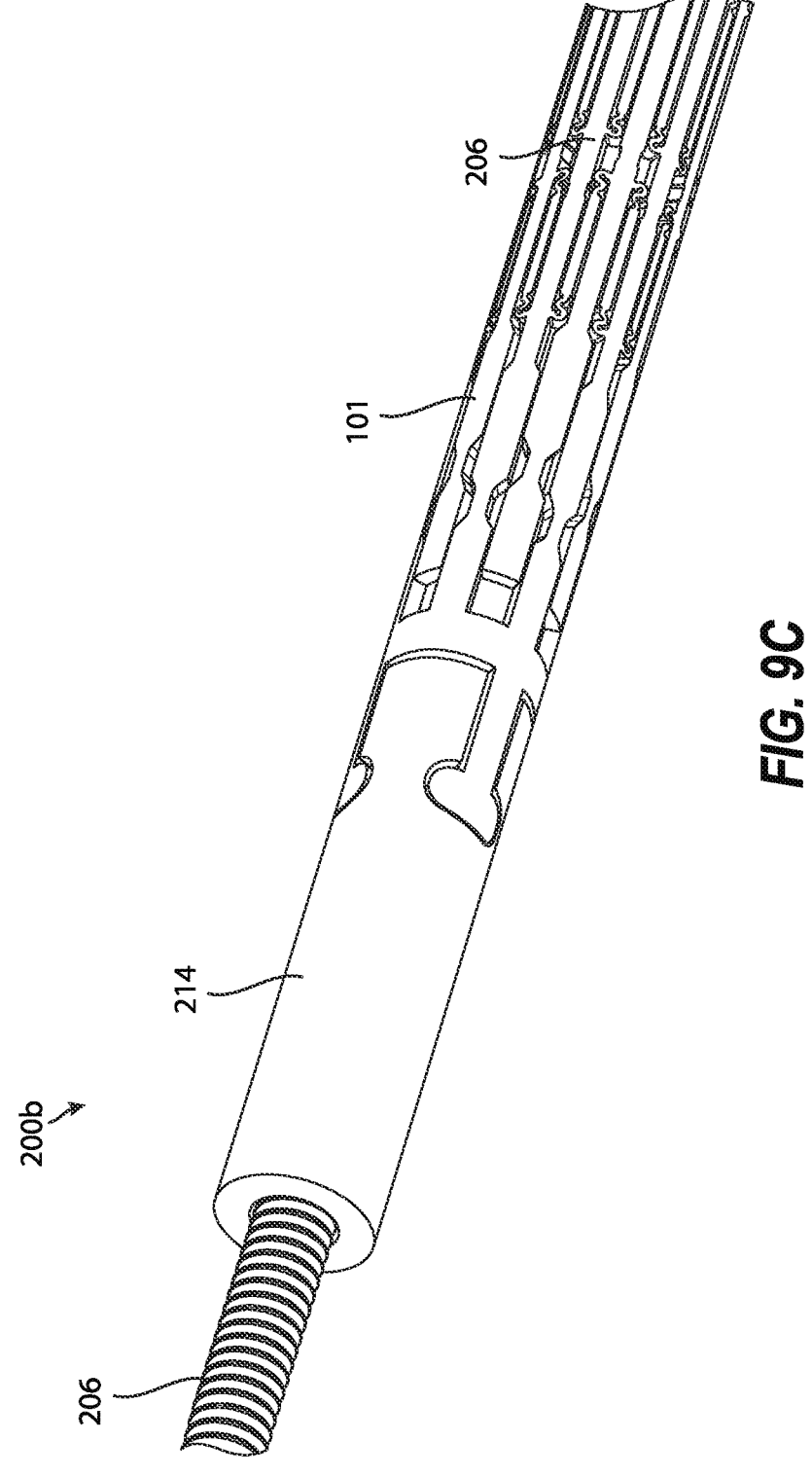

FIG. 9C is an enlarged view of the distal portion shown in FIGS. 9A and 9B but with the second elongated member 204 removed. As shown, the third elongated member 206 may extend through the second elongated member 206, the connector 214 (if used), and through the lumen of the expandable device in the collapsed configuration. A distal end region of the third elongated member 206 may be fixedly coupled to the second end portion 101b of the stent

101. As a result, relative axial movement between the second and third elongated members 204, 206 moves the end portions 101a, 101b of the stent 101 towards and away from one another, thereby causing the stent 101 to expand and collapse. In some embodiments, rotation of one or both of the second and third elongated member 204, 206 causes translation of the first and second end portions 101a, 101b, respectively. The rotation may cause translation of the first and second end portions 101a and 101b via a screw-thread mechanism or by other means.

The expandable devices and/or stents of the present technology may be configured for use in a variety of medical applications. For example, in some embodiments the expandable device 100 may configured for use in a valvuloplasty procedure. In such embodiments, the expandable device 100 may comprise a stent (such as stent 101, stent 1101, stent 1400, stent 1500, stent 1600, and/or some variation thereof) configured to be positioned in a collapsed state at a native valve annulus (such as any one of the four major heart valves) and transformed into an expanded configuration to press outwardly against the annular tissue to widen the native valve opening.

Figure 10:
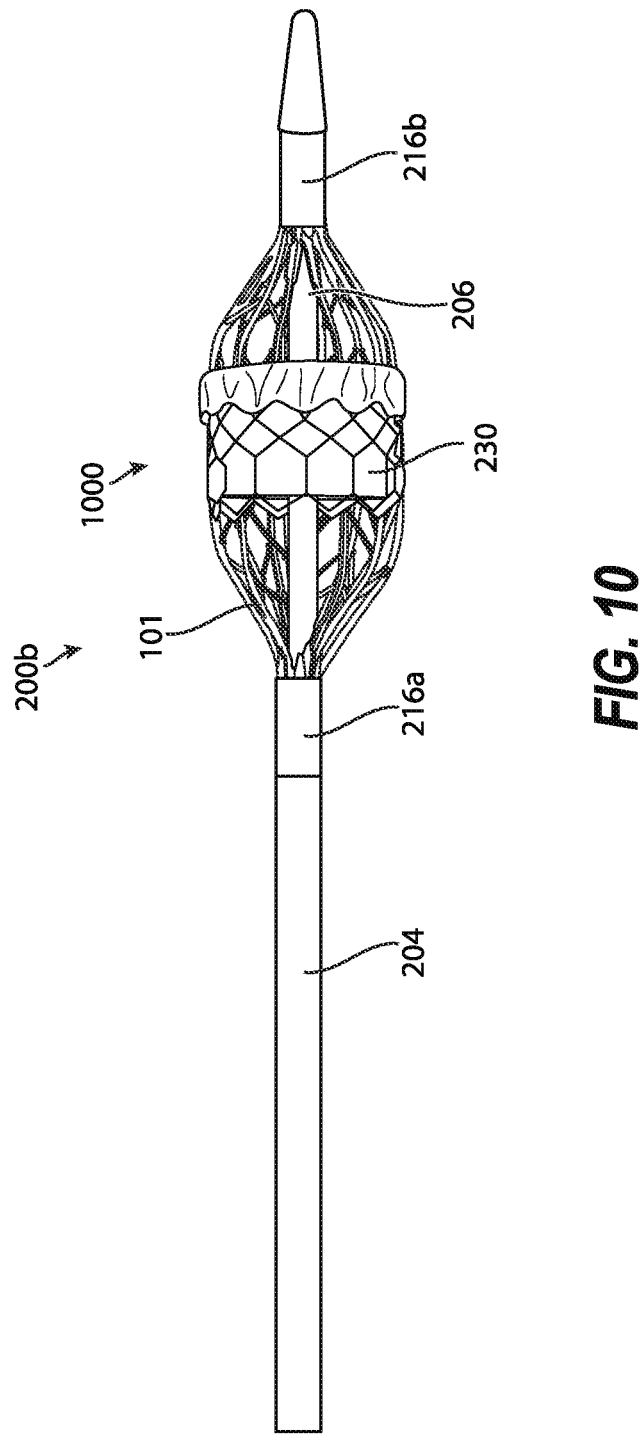
FIG. 10 depicts an expandable device comprising a replacement valve loaded on an expandable device configured in accordance with several embodiments of the present technology.

According to some embodiments, the expandable device 100 may be configured to facilitate deployment of a stent-valve (such as during a TAVR procedure). FIG. 10, for example, depicts an expandable device 1000 comprising a stent (such as stent 101, stent 1101, stent 1400, stent 1500, stent 1600, and/or some variation thereof) and a stent-valve 230 configured in accordance with several embodiments of the present technology. In FIG. 10, the expandable device 1000 is shown in an expanded configuration, mounted on a distal portion of a delivery device (such as delivery device 200). In some embodiments, the stent-valve 230 may be pre-loaded around an outer surface of the stent 101 such that the stent-valve 230 and the stent 101 are delivered to the native valve annulus together. When expanded at the treatment site, the expandable device 1000 pushes radially outwardly against an inner surface of the stent-valve 230, thereby forcing the stent-valve 230 to radially expand into apposition with the annular tissue. In some embodiments, the stent-valve 230 and the stent 101 are delivered and expanded separately. In some embodiments, the stent-valve 230 and the stent 101 are delivered on the same delivery device, but spaced longitudinally apart from one another to minimize the overall diameter of the system during placement into and through the vascular system. After placement into the vascular system but before deployment of the stent-valve 230 into the valve annulus, either the stent 101 or the stent-valve 230 is translated longitudinally on the delivery catheter to position the stent-valve 230 over the stent 101 for deployment.

According to some embodiments, the expandable device may comprise a stent (such as stent 101, stent 1101, stent 1400, stent 1500, stent 1600, and/or some variation thereof) and a cover positioned over all or a portion of the stent. For example, in some embodiments the expandable device may have a thin layer of material over all or a portion of the exterior surface of the stent. The cover may provide a protective barrier between the stent 101 and the stent-valve 230. Additionally or alternatively, the cover may extend proximally beyond a proximal or distal end of the stent 101 and function as a temporary valve.

In some aspects of the technology, the expandable device may comprise a stent (such as stent 101, stent 1101, stent 1400, stent 1500, stent 1600, and/or some variation thereof) and a valve positioned at a location along its length. The valve may be, for example, a one way valve. In some embodiments, it may be beneficial to position the valve at or near the proximal end of the expandable device and/or stent. For example, the expandable device may include a thin material extending proximally from the stent lumen to form a short wind-sock valve which opens to permit blood to flow due to differential blood pressure. When the pressure proximally is higher than the pressure distally, the valve flattens against the elongated member and impedes flow. Alternatively, if the expandable device is being placed in such a way that the desired direction of flow is proximally to distally, the valve could be reversed and placed on the distal end of the expandable device such that flow only proceeds distally. Additionally or alternatively, the expandable device and/or stent may include other types of valves, such as an iris valve, a multi-leaflet valve, a duckbill valve, and others. Moreover, the valve may be positioned at the distal end portion of the expandable device or at any location along the length of the expandable device.

According to some embodiments, the expandable devices and/or stents herein may be used for dilation of strictures or stents in the blood vessels (such as the aorta) or other body conduits and lumens such as the urethra, the esophagus, and the bile duct. Similarly, the expandable devices and/or stents may be configured for implantation within a body conduit to maintain the patency of the body conduit. According to several examples, the expandable device and/or stents herein may be used for temporary sealing of aortic ruptures, uncontrolled bleeding sites, aortic dissections, or other procedures where sealing the vessel while sustaining perfusion is desired. Additionally, the expandable devices and associated systems and methods of the present technology may be utilized in trans-septal as well as fenestrated aortic applications, where target vessel or lesion access requires navigation through tortuous anatomy. In such scenarios, the expandable device of the present technology allows for fixation adjacent to the target lesion or vessel.

According to some embodiments, the expandable devices and/or stents of the present technology are configured for permanent implantation into a body conduit. In these and other embodiments, the expandable device and/or stent may be configured so that the mechanism for translating the two ends of the expandable device closer to each other, such as a screw-thread mechanism, can maintain this translation permanently. According to some embodiments, the expandable device includes a coupler configured to be detachably coupled to an elongated member of a delivery system. According to some embodiments, the expandable devices and/or stents may comprise one or more valve elements, such as valve leaflets, a wind-sock or duckbill valve, or other valve, so that the expandable device and/or stent functions as a permanently implantable valve.

Figures 11A, 11B:
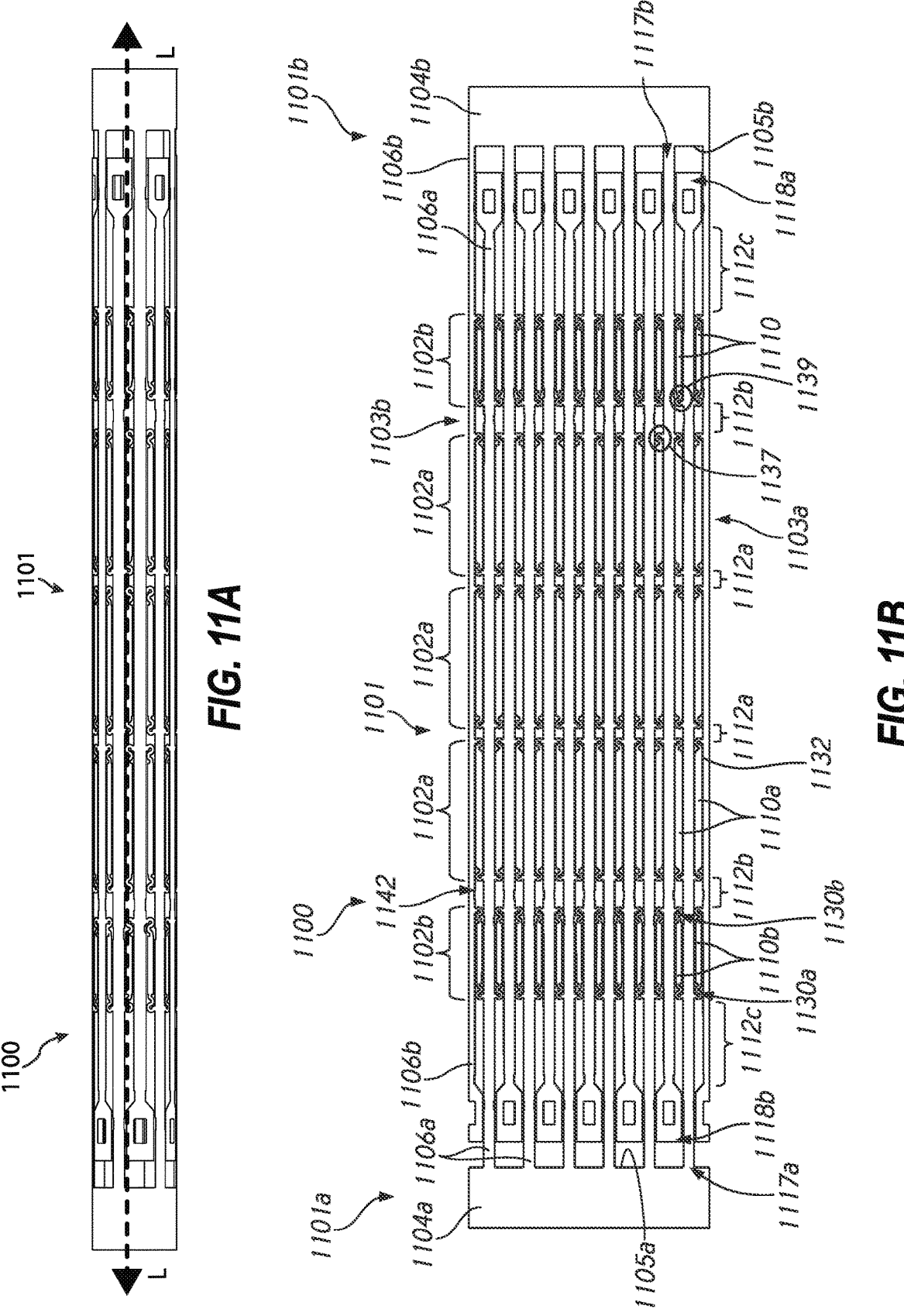
FIG. 11A is a side view of an expandable device of the present technology, shown in a collapsed configuration.
FIG. 11B is a side view of an expandable device of FIG. 11A in a laid-flat configuration.

FIG. 11A illustrates an expandable device 1100 configured in accordance with several embodiments of the present technology, shown in a collapsed (i.e., unexpanded) tubular configuration. For ease of explanation, FIG. 11B shows the expandable device 1100 as it would appear if, while in the collapsed configuration, it was cut longitudinally and then laid flat. The expandable device 1100 is configured to be delivered in the collapsed, tubular configuration to a treatment site within a body conduit, such as a blood flow passage, and radially expanded at the treatment site to treat or facilitate treatment of the body conduit.

Referring to FIGS. 11A and 11B, the expandable device 1100 may comprise a stent 1101 having a first end portion 1101a, a second end portion 1101b, and a length extending between the first and second end portions 1101a, 1101b along a longitudinal axis L (see FIG. 11A) of the expandable device 1100. The stent 1101 can comprise a plurality of longitudinally-extending spines 1106 and a plurality of struts 1110 extending between circumferentially adjacent spines 1106. The struts 1110 may be attached to the spines 1106 at flexible joints 1132. The spines 1106 may comprise first spines 1106a having fixed ends 1117a proximate the first end portion 1101a and free ends 1118a proximate the second end portion 1011b, and second spines 1106b having fixed ends 1117b proximate the second end portion 1101b and free ends 1118b proximate the first end portion 1101a. The free ends 1118a, 1118b allow the first and second spines 1106a, 1106b to slide axially relative to one another when the stent is axially compressed. The relative axial movement of the first and second spines 1106a, 1106b pushes/pulls the ends of the struts 1110 to force the struts 1110 out of alignment with the spines 1106. The struts 1110 push circumferentially adjacent spines away from one another as the struts 1110 angle away from the spines 1106, thereby increasing a diameter of the stent. As discussed in greater detail below, in some examples the expandable device 1100 may be configured to limit the axial movement of the spines 1106 such that once the stent has been axially compressed by a certain amount, the spines 1106 are prevented from sliding relative to one another and begin to bow or buckle outwardly under the axially compressive forces as well as the circumferentially expansive forces applied by the struts 1110.

As previously mentioned, the first and second spines 1106a, 1106b may have fixed ends and free ends. According to some embodiments, for example as shown in FIGS. 11A and 11B, the stent 1101 may comprise a first band 1104a at the first end portion 1101a and a second band 1104b at the second end portion 1101b. Each of the first and second bands 1104a, 1104b may comprise a length of the stent 1101 along which the stent 1101 is circumferentially continuous. The fixed ends 1117a of the first spines 1106a may be disposed at the first band 1104a and the fixed ends 1117b of the second spines 1106b may be disposed at the second band 1104b. As a result, the first band 1104a secures the fixed ends 1117a of the first spines 1106a relative to one another such that axial movement of the first band 1104a simultaneously translates the first spines 1106a, and the second band 1104b secures the fixed ends 1117b of the second spines 1106b relative to one another such that axial movement of the second band 1104b simultaneously translates the second spines 1106b.

In some embodiments, the stent 1101 does not include the first and/or second bands 1104a, 1104b and instead the fixed ends of the first spines 1106a and/or the fixed ends of the second spines 1106b may be fixed relative to one another by other means. For example, in some embodiments the fixed ends 1117a, 1117b of the first and/or second spines 1106a, 1106b may be welded, glued, or otherwise fixed to an elongated member, and/or crimped between a band and an underlying delivery member. In some embodiments, the fixed ends 1117a, 1117b of the first and/or second spines 1106a, 1106b may comprise eyelets, and a strand of material may be threaded through the eyelets, thereby coupling the fixed ends together. In some embodiments, the strand of material may also be coupled to a delivery member, such as an elongated rod or shaft.

According to some embodiments, for example as shown in FIGS. 11A and 11B, each of the free ends 1118a, 1118b may enclose an opening. The expandable device 1100 may include a flexible strand threaded through the openings to help maintain the free ends 1118a, 1118b in generally the same plane as they move longitudinally towards and away from the bands 1104a, 1104b. In some embodiments, a rigid, semi-rigid, or fabric annular ring with hooks, barbs, protrusions or other engagement features may engage with the openings in free ends 1118a or 1118b. In some embodiments, such a ring may be used to apply axial tension to the ends 1118a, 1118b in order to actuate the expansion phase dominated by lateral spine vs spine movement. This can be done in addition to axial compression, concurrently with axial compression or at a different time, or in isolation. In some embodiments, one, some, or all of the free ends 1118a, 1118b do not include an opening.

The first and second spines 1106a, 1106b may alternate about a circumference of the stent 1101 when in the tubular configuration such that no first spine 1106a is circumferentially adjacent another first spine 1106a and no second spine 1106b is circumferentially adjacent another second spine 1106b. In some embodiments, two or more first spines 1106a may be circumferentially adjacent about the circumference of the stent 1101 and/or two or more second spines 1106b may be circumferentially adjacent about the circumference of the stent 1101. The first spines 1106a may have the same length or different lengths, and the second spines 1106b may have the same length or different lengths. The first spines 1106a and the second spines 1106b may have the same length, or the first spines 1106a may have a first length and the second spines 1106b may have a second length different than the first length.

When the expanded device 1100 and/or stent 1101 is in the collapsed configuration, the free ends 1118a, 1118b of the spines 1106 may be spaced apart from the corresponding band 1104a, 1104b by an initial distance d1. As the stent 1101 radially expands and the spines 1106 move axially relative to one another, the free ends 1118a, 1118b move closer to the opposing surfaces 1105a, 1105b of the bands 1104a, 1104b and, eventually, contact the opposing surfaces 1105a, 1105b. As detailed herein, contact between the free ends 1118a, 1118b and the bands 1104a, 1104b axially compresses the spines 1106a, 1106b, thereby causing the spines 1106 to bow outwardly.

When the expanded device 1100 and/or stent 1101 is in a collapsed configuration, the free ends 1118a of the first spines 1106a are spaced apart from the second band 1104b by a first distance d1, and the free ends 1118b of the second spines 1106b are spaced apart from the first band 1104a by a second distance d2. The first distance d1 and the second distance d2 may be the same or different when the stent 1101 is in the collapsed configuration, and each is measured along a longitudinal dimension of the stent 1101. As a distance between the first and second bands 1104a, 1104b is decreased and the spines 1106 move axially relative to one another, the free ends 1118a, 1118b move closer to opposing surfaces 1105a, 1105b of the corresponding bands 1104a, 1104b, and, eventually, contact the opposing surfaces 1105a, 1105b (at the same time or different times), thereby stopping axial movement of the spine relative to the band. The opposing surfaces 1105a, 1105b of the bands 1104a, 1104b, for example, may face in a direction opposite that of the movement of the adjacent free end 1118a, 1118b such that the free end cannot move along the longitudinal axis L beyond the corresponding opposing surface and/or band. In some embodiments, the axial stop for the free ends may be a portion of the stent 1101 other than the bands 1104a, 1104b, and/or may be a component of the delivery system and/or other portion of the expandable device 1100. As detailed elsewhere herein, the interaction between the free ends 1118a, 1118b and the bands 1104a, 1104b (or other axial stop) axially compresses the spines 1106, thereby causing the spines 1106 to bow outwardly.

According to some embodiments, for example as shown in FIGS. 11A and 11B, the end portions of the struts 1110 may be coupled to the spines 1106 via joints 1132. Some or all of the struts 1110 may have a first end coupled to one of the spines 1106 and a second end coupled to a different one of the spines 1106. As such, some or all of the struts 1110 may extend between spines 1106 and may not directly connect to another strut 1110. In some embodiments, some or all of the struts 1110 may extend between circumferentially adjacent spines 1106 such that the spines 1106 and struts 1110 alternate about a circumference of the stent 1101. In some embodiments, the first end of one, some, or all of the struts 1110 is coupled to one of the first spines 1106a, and the second end of the strut(s) 1110 is coupled to one of the second spines 1106b. In some embodiments, the stent 1101 may include one or more spines 106 that are not connected to another spine 1106 by a strut 1110 and/or one or more spines 1106 that are not connected to a strut 1110.

Between the first and second end portions 1101a, 1101b, the stent 1101 may comprise a plurality of strut regions 1102 (labeled individually as 1102a and 1102b) and a plurality of spine regions 1112 (labeled individually as 1112a, 1112b, and 1112c), each of which extend about all or a portion of the circumference of the stent 1101. The strut regions 1102 may include a plurality of struts 1110, each separated by one or more spines 1106. Some or all of the strut regions 1102 can be disposed longitudinally between a pair of spine regions 1112, and some or all of the spine regions 1112 can be disposed longitudinally between a pair of strut regions 1102. In some embodiments, at least one spine region 1112 is positioned between all of the strut regions 1102 and the first and/or second end portions 1101a, 1101b and/or first and second bands 1104a, 1104b. Some or all of the strut regions 1102 can be connected to spine regions 1112 on opposing longitudinal sides of the strut region 1102. Likewise, some or all of the spine regions 1112 can be connected to strut regions 1102 on opposing longitudinal sides of the spine region 1112.

According to some embodiments, a first longitudinal end of each of the strut regions 1102 may be defined by a circumferential band composed of first pairs 1130a of joints 1132 facing towards the second end portion 1101b of the stent 1101 (i.e., the struts 1110 attached to the joints 1132 of the first pairs 1130a form a V-shape that opens in the direction of the second end portion 1101b), and a second longitudinal end of each of the strut regions 1102 may be defined by a circumferential band composed of second pairs 1130b of joints 1132 facing towards the first end portion 1101a of the stent 1101 (i.e., the struts 1110 attached to the joints 1132 of the second pairs 1130b form a V-shape that opens in the direction of the first end portion 101a). The first pairs 1130a of joints may be disposed along the first spines 1106a and the second pairs 1130b of joints may be disposed along the second spines 1106b.

The strut regions 1102 may be longitudinally adjacent one another along the length of the stent 1101 such that the band of first pairs 1130a of joints 1132 of a first one of the strut regions 1102 may be longitudinally adjacent the band of second pairs 1130b of joints 1132 of a longitudinally adjacent second strut region 1102.

The spines 1106 may extend longitudinally across one, some, or all of the strut regions 1102 such that each of the strut regions 1102 includes a coextending length of each of the spines 1106. In some embodiments, for example as shown in FIGS. 11A and 11B, the struts 1110 do not extend longitudinally across any of the spine regions 1112 and, as such, the spine regions 1112 may include only a portion of each spine 1106 and do not include any struts 1110.

At least when the stent 1101 is represented in a laid-flat view, such as in FIG. 11B, one, some, or all of the spines 1106 may be generally linear and substantially parallel to (a) the longitudinal axis L, (b) one, some, or all of the struts 1110, and/or (c) one, some, or all of the other spines 1106. In these and other embodiments, when the stent 101 is in the collapsed configuration, one, some, or all of the spines 1106 may be generally linear and substantially parallel to (a) the longitudinal axis L, (b) one, some, or all of the struts 1110, and/or (c) one, some, or all of the other spines 1106. As the stent begins to expand, portions of the spines 1106 will begin to bend as the intermediate regions of the spines 1106 move radially away from the longitudinal axis L while the fixed ends 1117*a*, 1117*b* remain radially fixed relative to the longitudinal axis L.

Some or all of the struts 1110 may be generally linear along all or a portion of their lengths, as shown in FIGS. 11A and 11B. At least when the stent is represented in a laid-flat view, such as in FIG. 11B, the struts 1110 may be generally linear and substantially parallel to (a) the longitudinal axis L, (b) one, some, or all of the spines 1106, and/or (c) the other struts 1110 within the same strut region 1102 and/or some or all of the other strut regions. In these and other embodiments, when the stent 1101 is in the collapsed configuration, the struts 1110 may be generally linear and substantially parallel to (a) the longitudinal axis L, (b) one, some, or all of the spines 1106, and/or (c) the other struts 1110 within the same strut region 1102 and/or some or all of the other strut regions. The struts 1110 may be generally linear and angled relative to the longitudinal axis L and/or angled with respect to one, some, or all of the spines 1106 when the stent 1101 is in an expanded configuration. In some embodiments, all or a portion of one or more of the struts 1110 may be curved when the stent is in a collapsed configuration and/or when the stent 1101 is in an expanded configuration. For example, the struts may not have hinges at their ends, and the longitudinal translation of spines may cause the struts to deform into an s-shape, which still circumferentially expands the stent as described herein.

In some embodiments, struts 1110 within different strut regions 1102 may have different lengths. For example, the stent may have one or more first strut regions 1102*a* with first struts 1110*a* having a first length and one or more second strut regions 1102*b* with second struts 1110*b* having a second length less than the first length. One or more of the first strut region(s) 1102*a* may be positioned at a more central region of the stent, and at least one second strut region 1102*b* may be positioned on either side of the first strut region(s) 1102*a* such that at least one second strut region 1102*b* (e.g., one, two, three, four, etc.) is between the first strut region(s) 1102*a* and the first end portion 1101*a* of the stent and at least one second strut region 1102*b* is between the first strut region(s) 1102*a* and the second end portion 1101*b* of the stent. When the stent is expanded, the longer first struts 1110*a* of the first strut region(s) 1102*a* push adjacent spines 1106 away from one another to a greater extent than do the shorter struts 1110*b* of the second strut regions 1102*b*, thereby forming tapered portions 1150*a*, 1150*b* of the stent in the expanded configuration (see FIG. 13).

In FIGS. 11A and 11B, the stent 1101 has three first strut regions 1102*a* and two second strut regions 1102*b*. In other embodiments, the stent 1101 may have more or fewer first strut regions 1102*a* (e.g., one first strut region, two first strut regions, four first strut regions, etc.) and/or more or fewer second strut regions 1102*b* (e.g., one second strut region, three second strut regions, four second strut regions, etc.). Likewise, the stent 1101 may have more than two strut regions 1102 having struts 1110 of different lengths. For example, the stent 1101 may have three, four, five, six, etc. strut regions 1102, each having a different strut length than the other strut regions 1102. In some embodiments, the struts 1110 of all of the strut regions 1102 have substantially the same length. In some embodiments, none of the struts 1110 have the same length.

According to some embodiments, for example as shown in FIGS. 11A and 11B, the stent 1101 may include spine regions 1112 having different lengths. The spine regions 1112 may comprise circumferential bands of the stent 1101 that do not include any struts 1110. In the example shown in FIGS. 11A and 11B, the stent 1101 includes first spine regions 1112*a*, second spine regions 1112*b*, and third spine regions 1112*c*, each having different lengths. The individual lengths of the first spine regions 1112*a* may be less than the individual lengths of the second spine regions 1112*b*, and the individual lengths of the second spine regions 1112*b* may be less than the individual lengths of the third spine regions 1112*c*. In some embodiments, the lengths of the first, second, and/or third spine regions 1112*a*, 1112*b*, 1112*c* may be substantially the same.

As shown in FIGS. 11A and 11B, the first spine regions 1112*a* may be positioned between adjacent first strut regions 1102*a*, the second spine regions 1112*b* may be positioned between the first strut regions 1102*a* and the second strut regions 1102*b*, and the third spine regions 1112*c* may be positioned between the second strut regions 1102*b* and the first and second end portions 1101*a*, 1101*b* and/or first and second bands 1104*a*, 1104*b*. In some embodiments, the first strut regions 1102*a* may abut one another such that the joints 1132 associated with the first strut regions 1102*a* axially abut or overlap one another when the stent is in a collapsed configuration. In such embodiments, the stent 1101 may not include any first spine regions 1112*a*, or the first spine regions 1112*a* may have a negligible length.

A width of one, some, or all of the spines 1106 may be constant along the entire length of the spine 1106. According to some embodiments, for example as shown in FIGS. 11A and 11B, the spines 1106 may include one or more reliefs or narrowed portions 1142 along their lengths and have a generally constant width therebetween. The stent 1101 may be configured to preferentially bend at the narrowed portions 1142 as the stent 1101 expands. In some embodiments, the narrowed portions 1142 are disposed at portion(s) of the spine(s) 1106 extending between strut regions 1102 (and not along portions coextensive with a strut region 1102). In some embodiments, the narrowed portions 1142 are disposed only between strut regions 1102 of different lengths (for example, within the second spine regions 1112*b*). According to some embodiments, for example as shown in FIGS. 11A and 11B, only the first spines 1106*a* have the narrowed portions 1142 (and not the second spines 1106*b*), or vice versa. Both the first and second spines 1106*a*, 1106*b* may have narrowed portions 1142. In some embodiments, the stent 1101 may be configured using localized wall thinning, localized heat treatment, localized chemical treatment, or other means to induce preferential bends at the desired location (such as location 1142) as the stent 1101 expands.

In some embodiments, a width of one, some, or all of the spines 1106 may vary along the length of the respective spine 1106. For example, one, some, or all of the spines 1106 may have a first width along the portion(s) of the spine 1106 coextensive with the strut regions 1102, and a second width along the portion(s) of the spines 1106 outside of the strut regions 1102. In some embodiments, a width of one, some, or all of the spines 1106 is constant along the length of the respective spine 1106.

In FIGS. 11A and 11B, the stent 1101 has two first spine regions 1112*a*, two second spine regions 1112*b*, and two third spine regions 1112*c*. In other embodiments, the stent 1101 may have more or fewer first spine regions 1112*a* (e.g., no first spine regions, one first spine region, three first spine regions, four first spine regions, etc.), more or fewer second spine regions 1112*b* (e.g., no second spine regions, one second spine region, three second spine regions, four second spine regions, etc.), and/or more or fewer third spine regions 1112*c* (e.g., no third spine regions, one third spine region, three third spine regions, four third spine regions, etc.). Additionally or alternatively, the stent 1101 may have more or fewer than three spine regions 1112 having different lengths. For example, the stent 1101 may have three, four, five, six, etc. spine regions, each having a different length than the other spine regions 1112. In some embodiments, all of the spine regions 1112 of the stent 1101 have substantially the same length. In some embodiments, none of the spine regions 1112 have the same length.

According to some embodiments, for example as shown in FIGS. 11A and 11B, the stent 1101 may have different joints along different spines 1106. The different joints may have different lengths, different geometries, different orientations, and/or other configurations. For example, the stent 1101 may include first pairs of joints 1130*a* between the first spines 1106*a* and the struts 1110 connected thereto and second pairs of joints 1130*b* between the second spines 1106*b* and the struts 1110 connected thereto. The first pairs of joints 1130*a* may face towards the free ends 1118*a* of the first spines 1106*a* and/or the second end portion 1101*b* of the stent 1101, and the second pairs of joints 1130*b* may face towards the free ends 1118*b* of the second spines 1106*b* and/or the first end portion 1101*a* of the stent 1101. As the stent 1101 moves from the collapsed configuration to the expanded configuration, the struts 1110 at the first pairs of joints 1130*a* may form a chevron or V-shape that opens towards the second end portion 1101*b* and the struts 1110 at the second pairs of joints 1130*b* may form a chevron or V-shape that opens towards the first end portion 1101*a*.

The joints 1132 may coincide with the first and second end portions of the struts 1110, or may extend from the first and second end portions of the struts 1110. The joints 1132 can have a width, thickness, and shape designed to allow the struts 1110 to swing away from the adjacent spines 1106 as the expandable device 1100 and/or stent 1101 radially expands, as well as to withstand the forces exerted on the struts 1110 by the spines 1106 as the ends of the spines 1106 and/or stent 1101 is axially compressed and as the stent is subjected to radial compressive forces.

The length, width, thickness, and/or geometry of each of the joints 1132 may be varied depending on the length of the strut 1110 to which the joint 1132 is attached or the angle through which the strut swings as the stent is expanded, as discussed in greater detail herein. One, some, or all of the individual joints 1132 may have a non-linear shape, such as a c-shape, an s-shape, a serpentine shape, a sinusoidal shape, a zig-zag shape, and/or any segment with one or more inflection points when the stent is in a collapsed configuration. In some embodiments, none, some, or all of the individual joints 1132 have the same shape. In some embodiments, none, some, or all of the individual joints 1132 have different shapes.

Figure 12A:
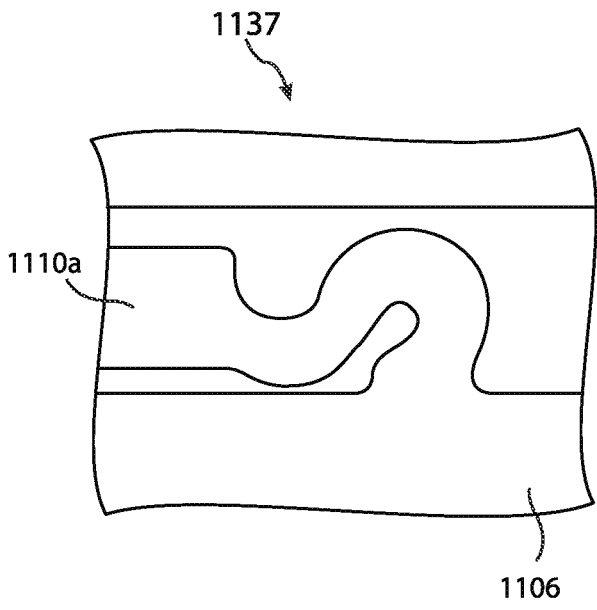
FIG. 12 is an enlarged view of a portion of the expandable device shown in FIGS. 11A and 11B.
Figure 12B:
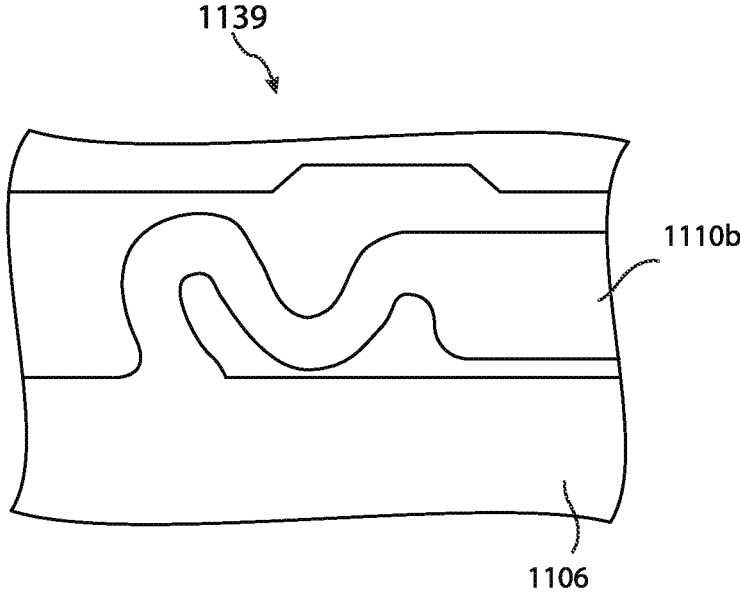
Figure 13:
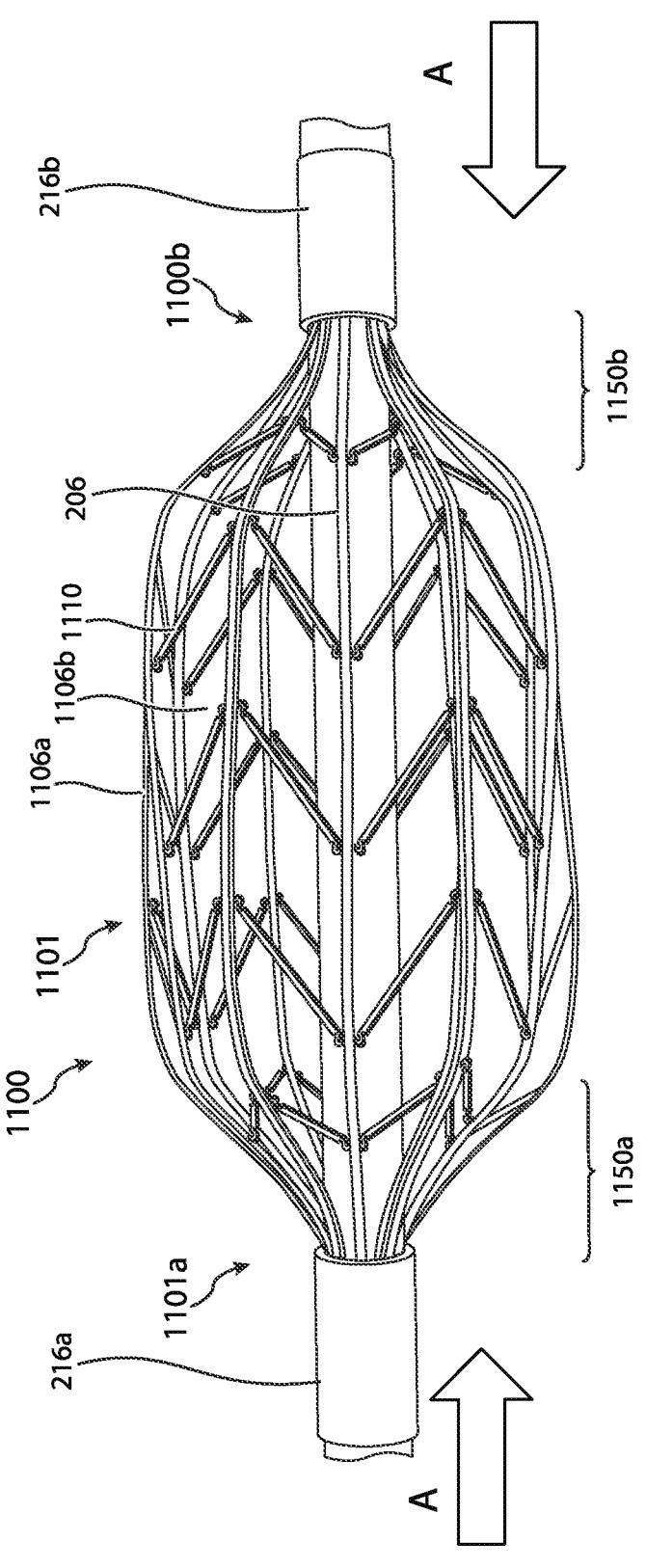
FIG. 13 depicts the expandable device of FIGS. 11A and 11B in an expanded state and coupled to a delivery system.

According to some embodiments, for example as shown in FIGS. 11A and 11B, the stent 1101 may have different joints in different strut regions 1102 and/or different joints depending on the length of the strut 1110 to which it is attached and/or the angle through which it swings. For example, the struts 1110*a* within the first strut regions 1102*a* may be coupled to the spines 1106 via first joints 1137, and the struts 1110*b* within the second strut regions 1102*b* may be coupled to the spines 1106 via second joints 1139. FIG. 12A is an enlarged view of one of the first joints 1137, and FIG. 12B is an enlarged view of one of the second joints 1139. As shown, the second joints 1139 may be longer and/or have more turns than the first joints 1137, as the second joints 1139 are coupled to the shorter struts 1110*a* which, in an expanded state, extend at an angle relative to the adjacent spines 1106 that is greater than the angle between the longer struts 1110*b* and the adjacent spines (see FIG. 13). As such, the second joints 1139 supporting the shorter struts 1110*a* may incorporate more turns in order to support that higher stress expected to be exerted on the second joints 1139 during expansion and collapse of the stent 1101 and/or once positioned in a body conduit.

Transformation of the stent 1101 between the collapsed configuration and the expanded configuration is substantially the same as described herein with respect to stent 101.

Figure 14:
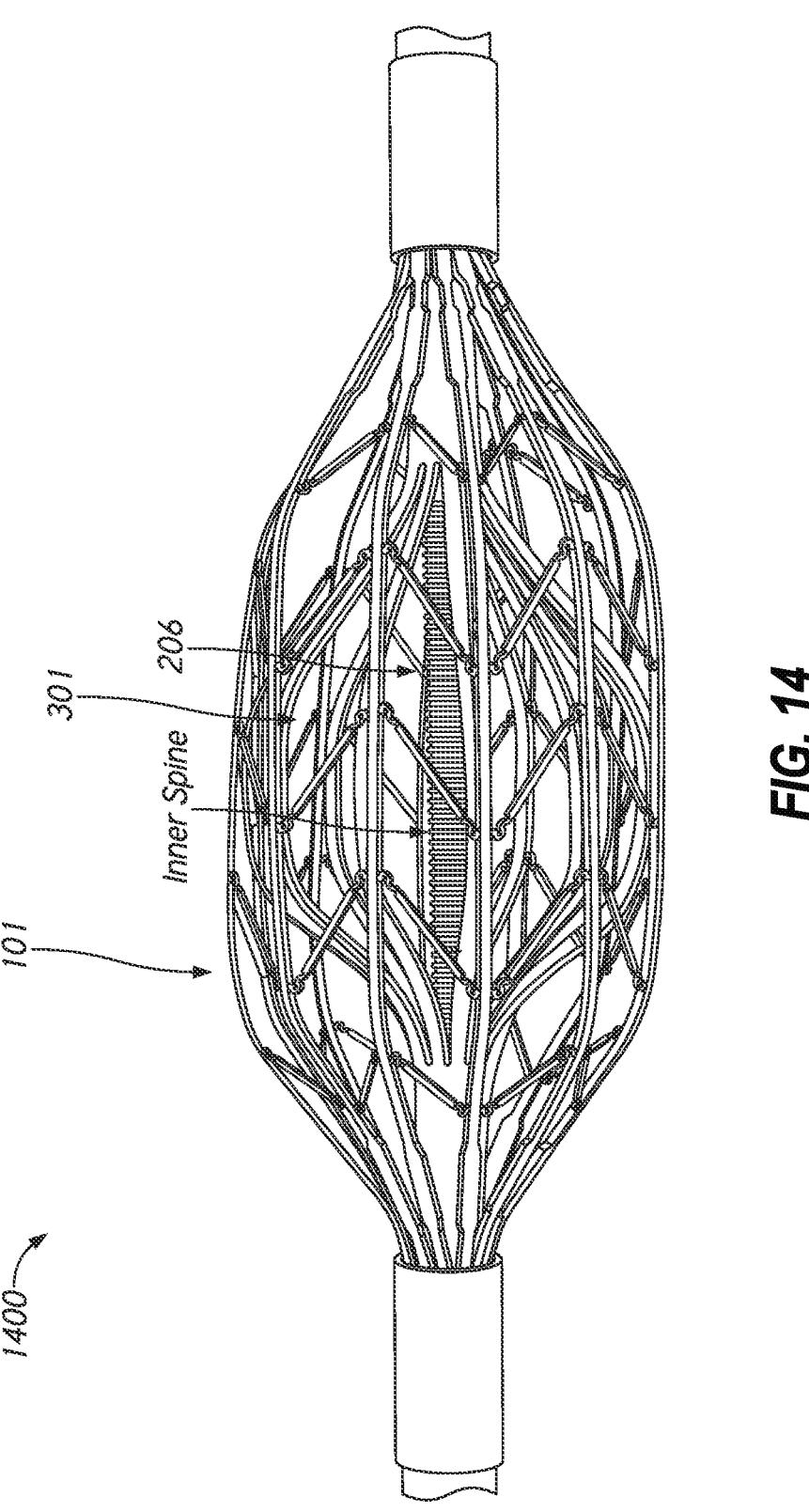
FIG. 14 illustrates an expandable device comprising outer and inner stents in accordance with embodiments of the present technology.

According to some aspects of the technology, the expandable device may comprise two or more nested stents. FIG. 14, for example, shows an expandable device 1400 comprising a first stent 101 and a second stent 300 positioned within a lumen of the first stent 100. The first stent 101 may be any of the stents described herein (such as stent 101, stent 1101, stent 1501, stent 1601, and/or some combination or variation thereof), and the second stent 300 may be any of the stents described herein (such as stent 101, stent 1101, stent 1501, stent 1601, and/or some combination or variation thereof). As shown, a length of the radially expanded portion of the inner, second stent 301 may be shorter than a length of the radially expanded portion of the outer stent 101 such that the tapering ends of the inner stent 301 do not overlap the tapered end portions of the outer stent 101. This way, the expanded portion of the inner stent 301 provides radial support to an intermediate region of the outer stent 101. In some embodiments, the expanded portions of the inner and outer stents 301, 101 may have substantially the same lengths and/or all or a portion of their respective tapered portions may overlap in the expanded configuration.

The inner and outer stents 301, 101 may have the same shape or different shapes in the expanded configuration. In some embodiments, one or both of the inner and outer stents 301, 101 have a substantially cylindrical shape between their respective tapered end portions. In some embodiments, one or both of the inner and outer stents 301, 101 have a more spherical or globular shape in the expanded configuration. The inner and outer stents 301, 101 may have the same number of spines or different numbers of spines. The spines of the inner stent 301 may have a different width and/or thickness than the spines of the outer stent 101. In these and other embodiments, the spines of the inner stent 301 may have the same width and/or thickness as the spines of the outer stent 101.

In many cases, it may be beneficial for the inner stent 301 to have the same number of spines or fewer spines than the outer stent 101 so that, at least in the expanded configuration, each of the spines of the inner stent 301 circumferentially align with a spine of the outer stent 101. That way, as the stents expand, the spines of the inner stent 301 push radially outwardly on the spines of the outer stent 101. In some embodiments, the inner spines may be coupled to the outer spines in one or more discrete locations to encourage such alignment.

Figure 15A:
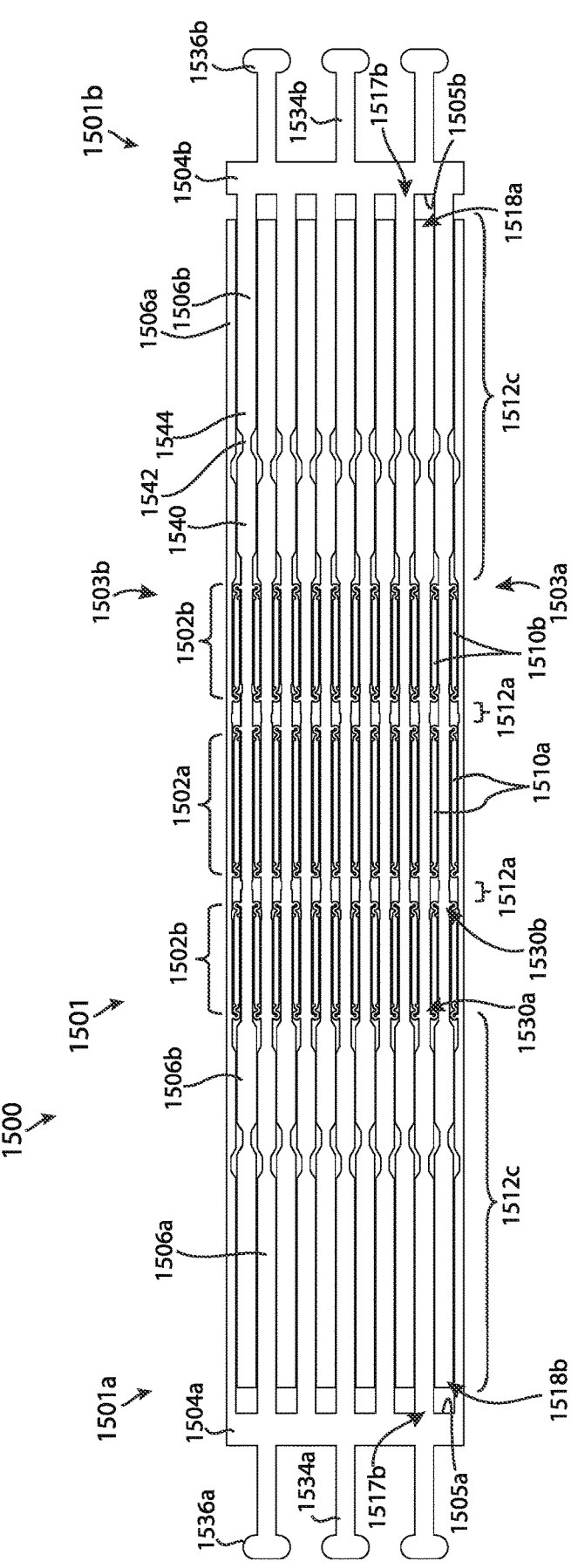
FIG. 15A is a laid flat configuration of an expandable device in accordance with the present technology.
Figures 15B, 15C:
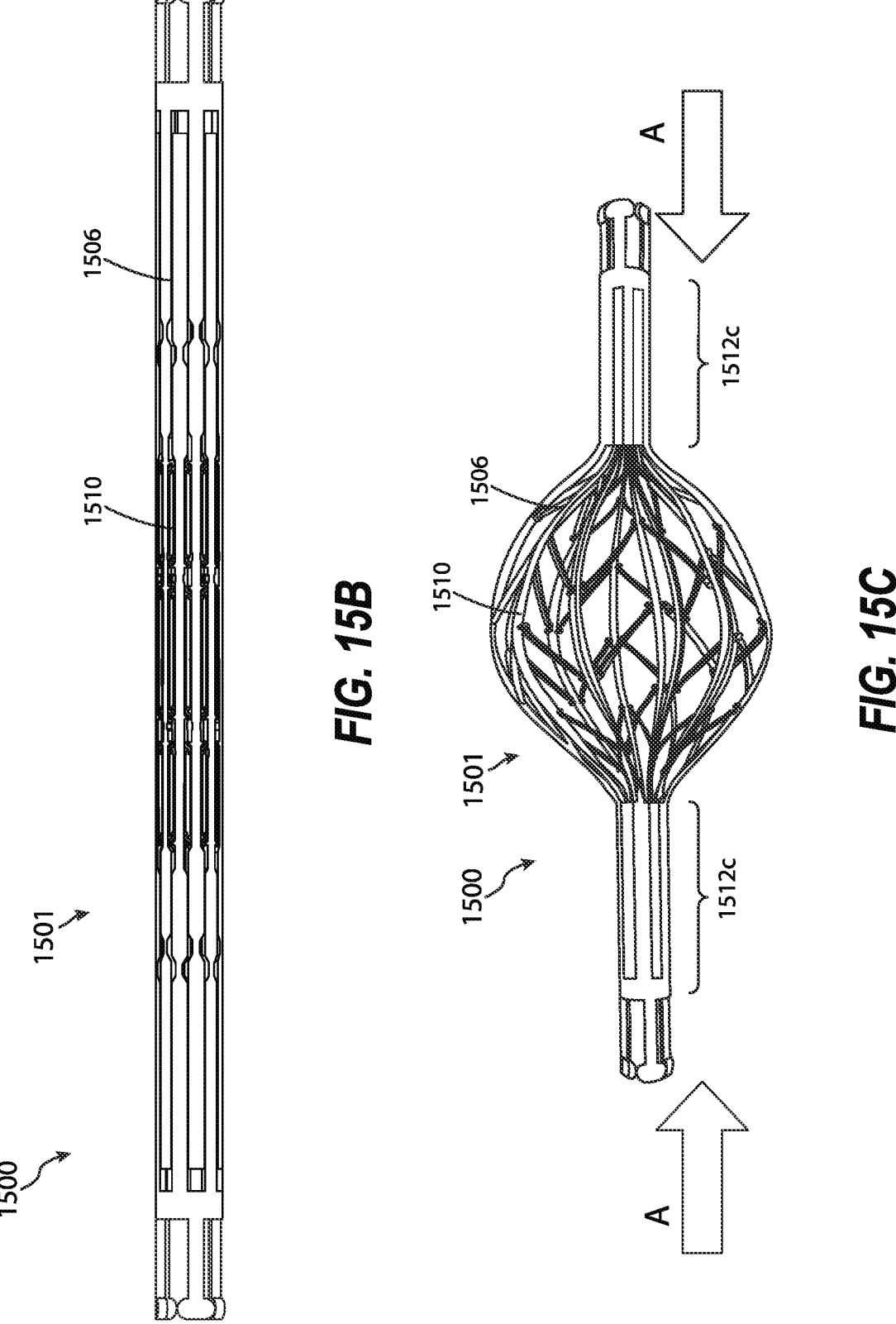
FIGS. 15B and 15C are side views of the expandable device of FIG. 15A shown in a tubular, collapsed configuration and a tubular, expanded configuration, respectively.

FIG. 15A is a laid flat configuration of an expandable device 1500 comprising a stent 1501 in accordance with several embodiments of the present technology. FIGS. 15B and 15C are side views of the expandable device 1500 shown in a tubular, collapsed configuration and a tubular, expanded configuration, respectively. The expandable device 1500 and/or stent 1501 may be configured to be positioned within the lumen of another expandable device (such as expandable device 100, 1100, 1600, etc.) and/or stent (such as stent 101, 1101, 1601, etc.), and/or may be configured to receive another expandable device and/or stent therein.

Except as detailed below, stent 1501 may be substantially the same as stent 101, with like numerals in FIGS. 15A-15C denoting like components. According to some embodiments, for example as shown in FIGS. 15A-15C, the stent 1501 may comprise a single first strut region 1502*a* and two second strut regions 1502*b*, each on either longitudinal side of the first strut region 1502*a*. The third spine regions 1512*c*, or the lengths of the spines 106 between the strut regions 1502 and end portions 1501*a*, 1501*b*, may be longer than the third spine regions 112*c* of stent 101, and the preferential bend regions 1542 may be farther from the end portions 1501*a*, 1501*b*. This way, should stent 1501 be positioned within stent 101, the two stents can be coupled at their respective ends to an actuating device (for example, for simultaneous actuation) without the tapered end portions of stent 1501 interfering with the tapered end portions of stent 101. The distance between alternating spines and the end ring may be substantially the same as that of outer stent 101 such that actuation of inner and outer stent occurs simultaneously. The distance between alternating spines and the end ring may be varied in order to have the inner stent actuate either before or after outer stent 101.

Figure 16A:
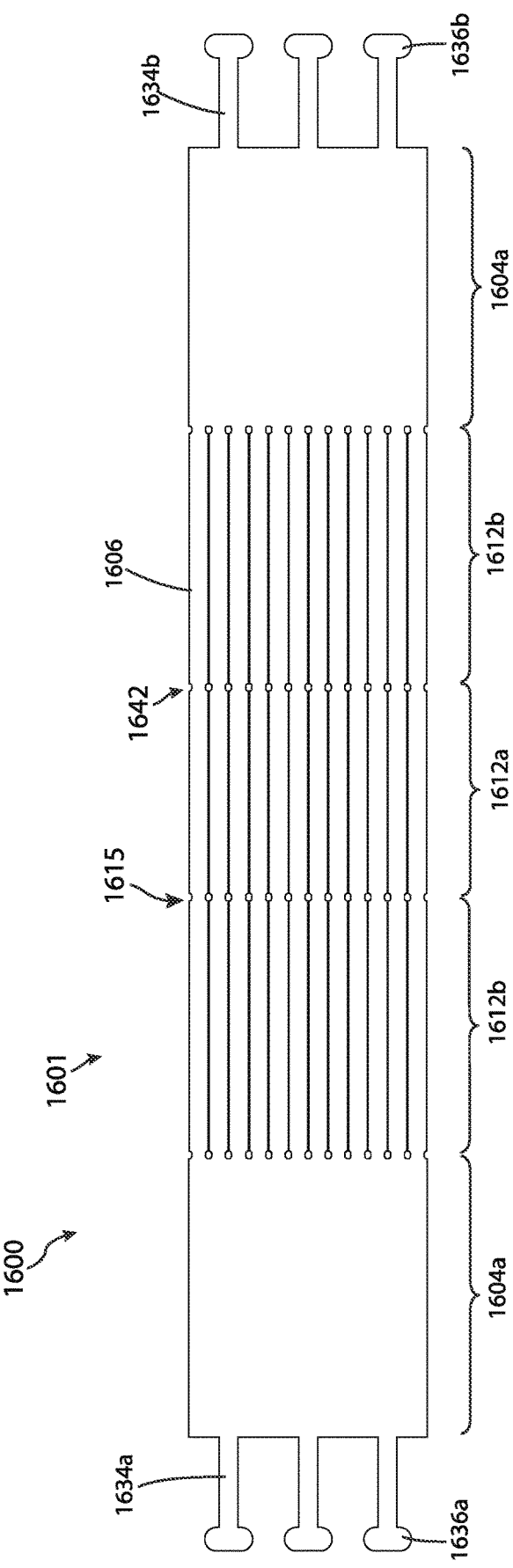
FIG. 16A is a laid flat configuration of an expandable device in accordance with the present technology.
Figures 16B, 16C:
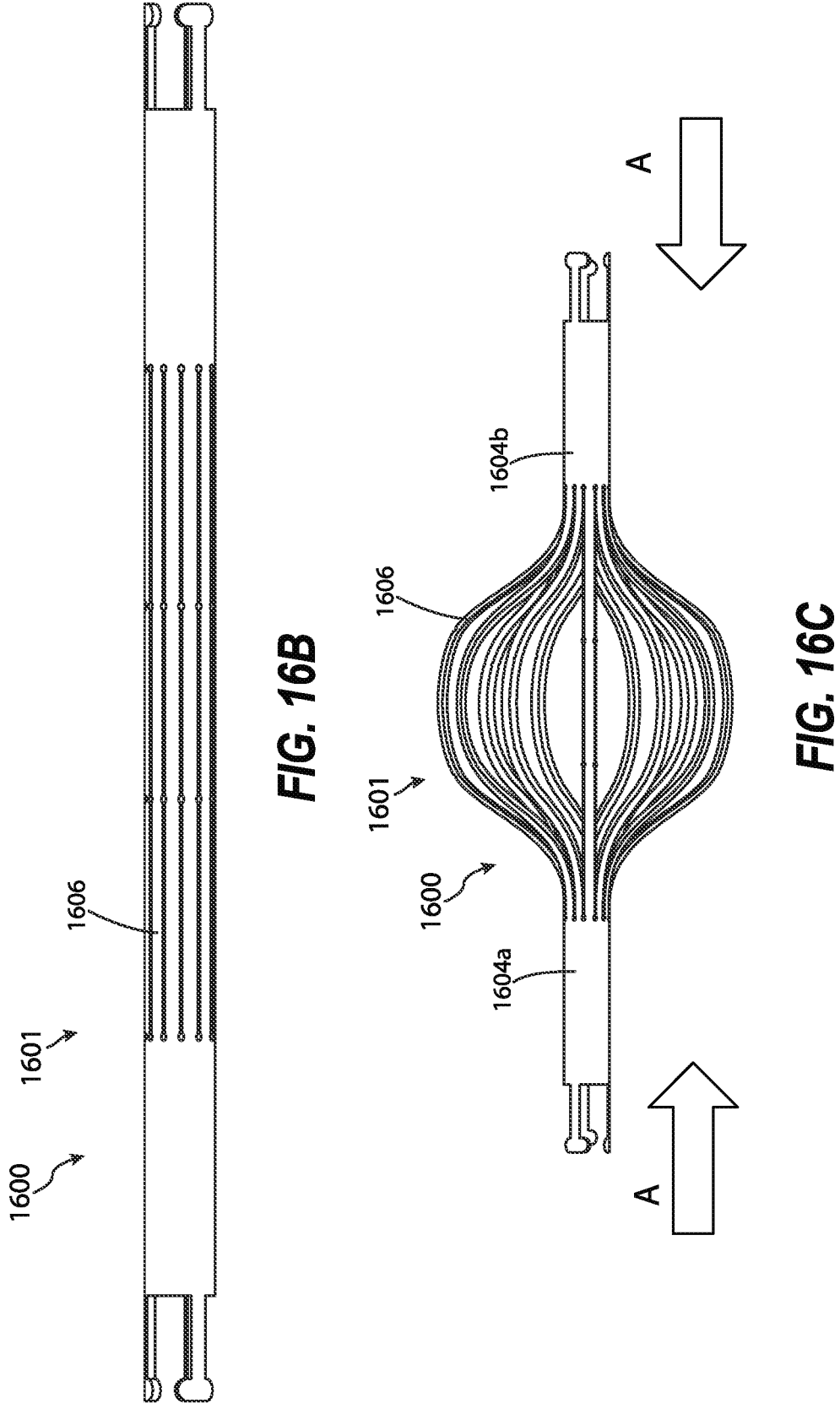
FIGS. 16B and 16C are side views of the expandable device of FIG. 16A shown in a tubular, collapsed configuration and a tubular, expanded configuration, respectively.

FIG. 16A is a laid flat configuration of an expandable device 1600 comprising a stent 1601 in accordance with several embodiments of the present technology, and FIGS. 16B and 16C are side views of the expandable device of FIG. 16A shown in a tubular, collapsed configuration and a tubular, expanded configuration, respectively. The expandable device 1600 and/or stent 1601 may be configured to be positioned within the lumen of another expandable device (such as expandable device 100, 1100, 1500, etc.) and/or stent (such as stent 101, 1101, 1501, etc.), and/or may be configured to receive another expandable device and/or stent therein.

Except as detailed below, stent 1601 may be substantially the same as stent 101, with like numerals in FIGS. 16A-16C denoting like components. According to some embodiments, for example as shown in FIGS. 16A-16C, the stent 1601 may not comprise any struts and may only include spines 1606 extending longitudinally between bands 1604*a*, 1604*b* at the first and second end portions 1601*a*, 1601*b*. In such embodiments, longitudinal compression of the stent 1601 simultaneously longitudinally compresses the spines 1606, thereby causing the spines 1606 to buckle radially outwardly into the expanded configuration. The stent 1601 may include one or more reliefs 1642 (FIG. 16A) that encourage the spines 1606 to assume a desired shape in the expanded configuration.

Figure 17A:
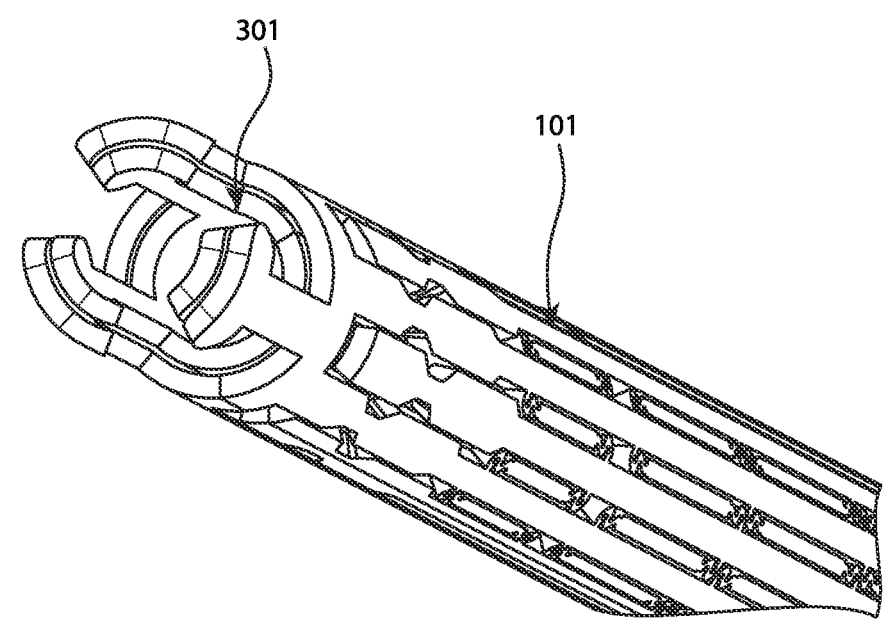
FIGS. 17A and 17B are isometric views of a portion of a treatment system in accordance with embodiments of the present technology.
Figure 17B:
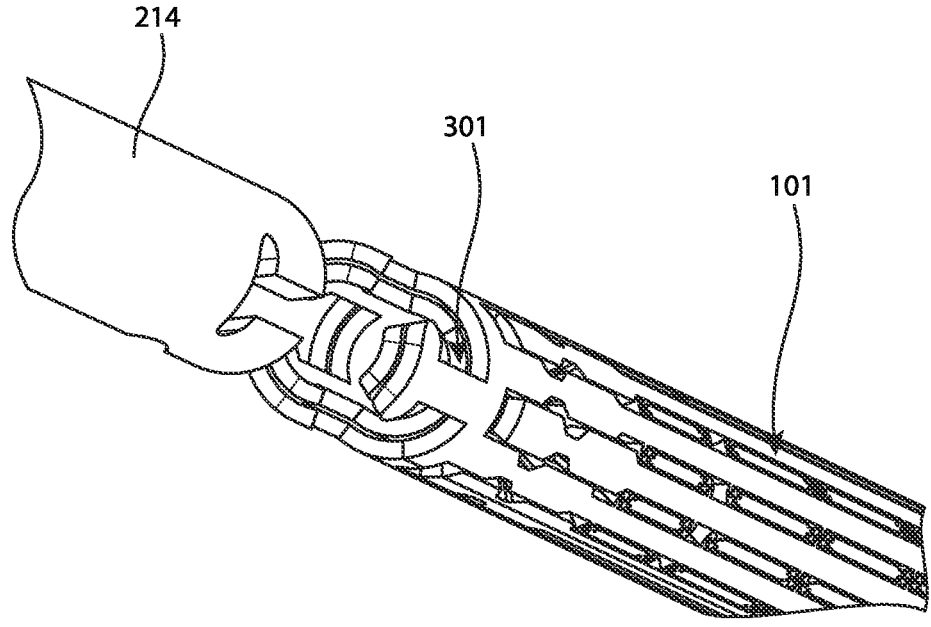

FIGS. 17A and 17B are isometric views of the first end portions of and inner and outer stent 301, 101 in accordance with embodiments of the present technology. As depicted, in some embodiments a single connector 214 may couple to both ends of the inner and outer stents 301, 101 (only one end portion depicted) so that both the inner and outer stents 301, 101 may be simultaneously longitudinally compressed and/or elongated. In some embodiments, the inner and outer stents 301, 101 are coupled to different actuation mechanisms and/or may be independently deployed.

Example Methods of Manufacturing

The expandable devices and/or stents of the present technology may be formed by one or more methods. In some examples the expandable device may be formed by laser-cutting a desired pattern into a tubular sheet of material. In some embodiments, the stent may be initially formed as a flat sheet of material having a pattern of struts and spines. The struts and spines may be formed by depositing a thin film on a flat surface in the desired pattern, or by laser-cutting a desired pattern into the flat sheet of material. The flat pattern may then be curled up into a generally tube-like shape (not shown) such that the longitudinal edges of the pattern are positioned adjacent to or in contact with one another. The longitudinal edges can be joined (e.g., via laser welding) along all or a portion of their respective lengths. In some embodiments, the struts and spines may be formed by depositing a thin film on the surface of a tubular frame in a desired pattern (e.g., via thin film deposition, vapor deposition, or combinations thereof).

In any of the foregoing methods of manufacture, the resulting stent and/or portions thereof (such as the struts and/or spines) may have a wall thickness of about 0.2 mm to about 0.6 mm, of about 0.3 mm to about 0.5 mm, of about 0.3 mm to about 0.4 mm, greater than about 0.2 mm, greater than about 0.3 mm, greater than about 0.4 mm, greater than about 0.5 mm, or greater than about 0.6 mm. As used herein to describe a dimension of the stent wall, "thickness" or "wall thickness" refers to a distance measured in a radial direction between the luminal and abluminal surfaces of the stent. The wall thickness of the stent may be, for example, generally equivalent to the thickness of the sheet or tube of material from which the stent is cut.

In other medical applications, the resulting stent and/or portions thereof may have a much larger or smaller wall thickness. For example, if the device is being placed in a tube or pipe, the wall thicknesses may be much larger. The stent struts, spines, or portions thereof may also have hinges at certain points, rather than depending upon elastic or plastic deformation of the struts or spines as the stent is expanded. In addition to superelastic nitinol, the devices may be made from steel, aluminum, polymers, carbon fibers, or composite combinations thereof.

According to several embodiments, all or a portion of the expandable device and/or stent may be heat treated in its desired fully expanded configuration, or in a configuration having a diameter smaller than is intended when the stent is implanted. Heat treating the stent may be beneficial for preferential bending at certain locations and may reduce or substantially remove any stresses that accompany forcing the stent from its collapsed or unexpanded configuration into the expanded configuration.

In some embodiments, a width and/or thickness of one or more of the struts and/or spines may be thinned to form one or more preferential bending locations to encourage the stent to expand to a desired shape.

CONCLUSION

Although many of the embodiments are described above with respect to systems, devices, and methods for treating cardiac disease, the technology is applicable to other medical applications and/or other approaches, such as pulmonary, gastrointestinal, or cerebral applications. The embodiments described herein may also be used for other applications, such as aerospace applications where strength, light weight, strength-weight ratio, low collapsed profile and simplicity of actuation are at a premium. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 2A-17B.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

We claim:

1. A stent comprising:
    a first end portion, a second end portion, and a longitudinal axis extending therebetween, the stent having a collapsed configuration for delivery through a delivery device to a treatment site in a body conduit and an expanded configuration; and a plurality of spines extending along the longitudinal axis, each of the spines extending between a first fixed end and a second free end, wherein axial compression of the stent in the collapsed configuration by a first distance causes the spines to move radially away from the longitudinal axis without axially compressing the spines, and wherein continued axial compression of the stent beyond the first distance simultaneously axially compresses the spines, thereby increasing the diameter of the stent.

2. The stent of claim 1, further comprising a plurality of struts, each of the struts extending between and connecting circumferentially adjacent spines.

3. The stent of claim 2, wherein none of the struts connect directly to another strut.

4. The stent of claim 1, the spines comprising first spines and second spines configured to move in opposing axial directions as the stent expands, the stent further comprising a plurality of struts, each of the struts extending between and connecting one of the first spines to one of the second spines.

5. The stent of claim 4, wherein each of the struts has a first end connected to one of the first spines and a second end connected to one of the second spines, and wherein, when the first spines and the second spines move axially relative to one another, each of the struts angles away from the corresponding one of the first spines and corresponding one of the second spines, thereby pushing the one of the first spines away from the one of the second spines and increasing a radial distance of the first and second spines from the longitudinal axis of the stent.

6. The stent of claim 1, wherein the stent comprises:
    a first strut region comprising a plurality of first struts, the first strut region extending about a circumference of the stent at a first axial location along the stent, and
    a second strut region comprising a plurality of second struts, the second strut region extending about a circumference of the stent at a second axial location longitudinally spaced apart from the first axial location, wherein the second struts are shorter first the second struts.

7. The stent of claim 6, wherein the stent comprises a plurality of first strut regions, and wherein (a) at least one of the first strut regions is positioned between the second strut region and the first end portion of the stent, and (b) at least another one of the first strut regions is positioned between the second strut region and the second end portion of the stent.

8. The stent of claim 6, wherein the stent comprises a plurality of first strut regions and a plurality of second strut regions, and wherein (a) at least one of the first strut regions is positioned between the second strut regions and the first end portion of the stent, and (b) at least another one of the first strut regions is positioned between the second strut regions and the second end portion of the stent.

9. The stent of claim 6, wherein the stent comprises a plurality of first strut regions and a plurality of second strut regions, and wherein (a) at least one of the first strut regions is positioned between the second strut regions and the first end portion of the stent, (b) at least another one of the first strut regions is positioned between the second strut regions and the second end portion of the stent, and (c) none of the first strut regions are disposed between two of the second strut regions.

10. The stent of claim 6, wherein the first strut region and the second strut region includes a portion of a spine coextensive with the struts within the respective region.

11. The stent of claim 6, the spines comprising first spines and second spines configured to move in opposing axial directions as the stent expands, wherein each of the first spines and each of the second spines spans both the first strut region(s) and the second strut region(s).

12. The stent of claim 1, the spines comprising first spines and second spines configured to move in opposing axial directions as the stent expands, wherein— each of the first spines has a fixed end proximate the first end portion of the stent and a free end proximate the second end portion, each of the second spines has a fixed end proximate the second end portion of the stent and a free end proximate the first end portion, and the stent comprises:

a first stop at the first end portion, wherein the first stop is configured to prevent axial movement of the free ends of the second spines proximally beyond the first stop, a second stop at the second end portion, wherein the second stop is configured to prevent axial movement of the free ends of the first spines distally beyond the second stop.

13. The stent of claim 12, wherein, when the stent is axially compressed such that the free ends of the first spines contact the second stop and the free ends of the second spines contact the first stop, additional axial compression of the stent causes the first and second spines to bow outwardly.

14. The stent of claim 1, the spines comprising first spines and second spines configured to move in opposing axial directions as the stent expands, wherein— each of the first spines has a fixed end portion and a free end portion;

each of the second spines has a fixed end portion and a free end portion, and wherein, when the first and second spines move axially relative to one another, the free end portions of the first spines move closer to the fixed end portions of the second spines, or vice versa, the free end portions of the second spines move closer to the fixed end portions of the first spines, or vice versa.

15. The stent of claim 1, the spines comprising first spines and second spines configured to move in opposing axial directions as the stent expands, wherein— each of the first spines has a fixed end portion proximate the first end portion of the stent and a free end portion proximate the second end portion;

each of the second spines has a fixed end portion proximate the second end portion and a free end portion proximate the first end portion, and wherein, when the first and second spines move axially relative to one another, the free end portions of the first spines move closer to the second end portion of the stent, or vice versa, the free end portions of the second spines move closer to the first end portion of the stent, or vice versa.

16. The stent of claim 1, the spines comprising first spines and second spines configured to move in opposing axial directions as the stent expands, wherein the first spines are fixed relative to the first end portion of the stent along an axial dimension.

17. The stent of claim 1, the spines comprising first spines and second spines configured to move in opposing axial directions as the stent expands, wherein the second spines are fixed relative to the second end portion of the stent along an axial dimension.

18. The stent of claim 1, the spines comprising first spines and second spines configured to move in opposing axial directions as the stent expands, wherein the first spines are fixed relative to the first end portion of the stent along an axial dimension and the second spines are fixed relative to the second end portion of the stent along the axial dimension.

19. The stent of claim 1, the spines comprising first spines and second spines configured to move in opposing axial directions as the stent expands, wherein the stent includes a band at the first end portion, wherein the band is continuous with the first spines.

20. The stent of claim 1, the spines comprising first spines and second spines configured to move in opposing axial directions as the stent expands, wherein the stent includes a band at the first end portion, wherein the first spines are fixed relative to the band.

21. The stent of claim 1, the spines comprising first spines and second spines configured to move in opposing axial directions as the stent expands, wherein the stent includes a band at the second end portion, wherein the band is continuous with the second spines.

22. The stent of claim 1, the spines comprising first spines and second spines configured to move in opposing axial directions as the stent expands, wherein the stent includes a band at the second end portion, wherein the second spines are fixed relative to the band.

23. The stent of claim 1, wherein, when the stent is in an expanded configuration, a diameter of the stent tapers in the direction of the first end portion.

24. The stent of claim 1, wherein, when the stent is in an expanded configuration, a diameter of the stent tapers in the direction of the second end portion.

25. The stent of claim 1, wherein, when the stent is in an expanded configuration, a diameter of the stent tapers in the direction of the first end portion and in the direction of the second end portion.

26. The stent of claim 1, wherein the stent has been heat treated to have a preset shape in an intermediate expanded configuration.

27. The stent of claim 1, wherein the stent has been heat treated to have a preset shape in a fully expanded configuration.

28. The stent of claim 1, wherein the stent further includes a cover extending over all or a portion of the stent.

29. The stent of claim 1, wherein the stent is formed of a laser cut sheet of material or a laser cut tube.

30. The stent of claim 1, wherein the stent is not a braid.

31. The stent of claim 1, wherein the first and second spines alternate about the circumference of the stent.

32. The stent of claim 1, wherein decreasing a longitudinal distance between the first end portion and the second end portion causes the circumferentially adjacent spines to move away from one another.

* * * * *